(12) United States Patent
Breitenbach-Koller et al.

(10) Patent No.: US 11,959,145 B2
(45) Date of Patent: Apr. 16, 2024

(54) METHOD FOR IDENTIFYING INTERVENTIONS THAT CONTROL THE TRANSLATIONAL ACTIVITY OF RIBOSOMAL PROTEINS IN DIFFERENTIAL MRNA EXPRESSION

(75) Inventors: Hannelore Breitenbach-Koller, Salzburg (AT); Helmut Hintner, Salzburg (AT); Johann Bauer, Salzburg (AT); Olaf Haubenreisser, Salzburg (AT)

(73) Assignees: Hannelore Breitenbach-Koller, Salzburg (AT); Helmut Hintner, Salzburg (AT); Johann Bauer, Salzburg (AT)

( * ) Notice: Subject to any disclaimer, the term of this patent is extended or adjusted under 35 U.S.C. 154(b) by 471 days.

(21) Appl. No.: 13/320,172

(22) PCT Filed: May 12, 2010

(86) PCT No.: PCT/EP2010/002941
§ 371 (c)(1),
(2), (4) Date: Jan. 23, 2012

(87) PCT Pub. No.: WO2010/130447
PCT Pub. Date: Nov. 18, 2010

(65) Prior Publication Data
US 2012/0134983 A1    May 31, 2012

(30) Foreign Application Priority Data
May 13, 2009    (EP) .................................... 09006497

(51) Int. Cl.
*C12N 15/63* (2006.01)
*C12Q 1/6883* (2018.01)
*C12Q 1/6897* (2018.01)

(52) U.S. Cl.
CPC ......... *C12Q 1/6897* (2013.01); *C12Q 1/6883* (2013.01); *C12Q 2600/136* (2013.01); *C12Q 2600/158* (2013.01)

(58) Field of Classification Search
None
See application file for complete search history.

(56) References Cited

FOREIGN PATENT DOCUMENTS

| WO | WO 99/20797 | 4/1999 |
|---|---|---|
| WO | WO 99/61600 | 12/1999 |
| WO | WO 00/32619 | 6/2000 |
| WO | WO 01/44516 | 6/2001 |
| WO | WO 2007/083094 | 7/2007 |
| WO | WO 2007/112965 | 10/2007 |
| WO | WO 2007/117438 | 10/2007 |

OTHER PUBLICATIONS

Yelick et al. (Rare Diseases, 2015, vol. 3, No. 1, pp. 1-11).*
Gopanenko et al (International Journal of Molecular Sciences, 2021, vol. 2, 4531, pp. 1-16) (Year: 2021).*
Fine (Fine Orphanet Journal of Rare Diseases 2010, vol. 5, No. 12, pp. 1-17) (Year: 2010).*
Gibson et al., "A Novel Method for Real Time Quantitative RT-PCR," Oct. 1, 1996, *Genome Research*, vol. 6, No. 10, p. 995-1001, Cold Spring Harbor Laboratory Press, Woodbury, NY.
Mueller et al., "A ribosomal protein is required for translational regulation of GCN4 mRNA. Evidence for involvement of the ribosome in eIF2 recycling," Dec. 4, 1998, *The Journal of Biological Chemistry*, vol. 273, No. 49, p. 32870-32877.
Nakajima et al., "Bidirectional role of orphan nuclear receptor RORalpha in clock gene transcriptions demonstrated by a novel reporter assay system," May 7, 2004, *FEBS Letters*, vol. 565, No. 1-3, p. 122-126, Amsterdam.
Pan et al., "A negative feedback loop of transcription factors that controls stem cell pluripotency and self-renewal," Aug. 1, 2006, *The FASEB Journal*, vol. 20, No. 10, p. 1730-1732, Fed. Of American Soc. For Experimental Biology, US.
Salas-Marco et al., "Discrimination Between Defects in Elongation Fidelity and Termination Efficiency Provides Mechanistic Insights into Translational Readthrough," May 13, 2005, *The Journal of Biological Chemistry*, vol. 348, No. 4, p. 801-815, Academic Press, United Kingdom.
"SiCHECK™ Vectors," Technical Bulletin Promega—XP-002292967, Feb. 12, 2004, No. 329, p. 1-17.
Su et al., "A dual reporter gene based system to quantitate the cell fusion of avian influenza virus H5N1," Sep. 6, 2007, *Biotechnology Letters*, vol. 30, No. 1, p. 73-79, Springer Netherlands, Dordrecht.
Chiocchetti et al., "Ribosomal proteins Rpl10 and Rps6 are potent regulators of yeast replicative life span", *Experimental Gerontology*, 2007, vol. 42, No. 4, pp. 275-286.
Darling et al., "Cycloheximide Facilitates the Identification of Aberrant Transcripts Resulting from a Novel Splice-Site Mutation in COL17A1 in a Patient with Generalized Atrophic Benign Epidermolysis Bullosa", *Journal of Investigative Dermatology*, 1998, vol. 110, No. 2, pp. 165-169.

(Continued)

*Primary Examiner* — Celine X Qian
(74) *Attorney, Agent, or Firm* — SALIWANCHIK, LLOYD & EISENSCHENK

(57) ABSTRACT

The present invention relates to systems and methods for screening compounds and/or mutant ribosomal proteins in a eukaryotic cell that increase or decrease the translation of a target gene and thereby ameliorate or revert a defective and/or undesired translation of a target gene. Disclosed are compounds and proteins as identified with the methods and systems of the invention, pharmaceutical and cosmetic compositions thereof, their uses for the preparation of a medicament, methods of treatment of a disease or condition or cosmetic condition related to the defective translation of a gene, for example genetic diseases such as Epidermolysis bullosa, as well as diagnostic measures practical for the clinical evaluation of such diseases or conditions. Also, kits are provided which comprise the identified compounds and/or proteins in addition to suitable means for performing the methods of the invention.

10 Claims, 17 Drawing Sheets
Specification includes a Sequence Listing.

(56) References Cited

OTHER PUBLICATIONS

Pachler et al., "Functional interaction in establishment of ribosomal integrity between small subunit protein rpS6 and translational regulator rpL10/Grc5p", *FEMS Yeast Research*, vol. 5, No. 3, pp. 271-280.
Thompson et al., "Replacement of the L11 binding region within *E.coli* 23S ribosomal RNA with its homologue from yeast: in vivo and in vitro analysis of hybrid ribosomes altered in the GTPase centre", *The EMBO Journal*, 1993, vol. 12, No. 4, pp. 1499-1504.
Uchiumi et al., "Replacement of L7/L12.L10 Protein Complex in the *Escherichia coli* Robosomes with the Eukaryotic Counterpart Changes the Specificity of Elongation Factor Binding", *The Journal of Biological Chemistry*, 1999, vol. 274, No. 39, po. 27578-27582.
Welch et al., "PTC124 targets genetic disorders caused by nonsense mutations", *Nature*, 2007, vol. 447, No. 7140, pp. 87-93.

\* cited by examiner

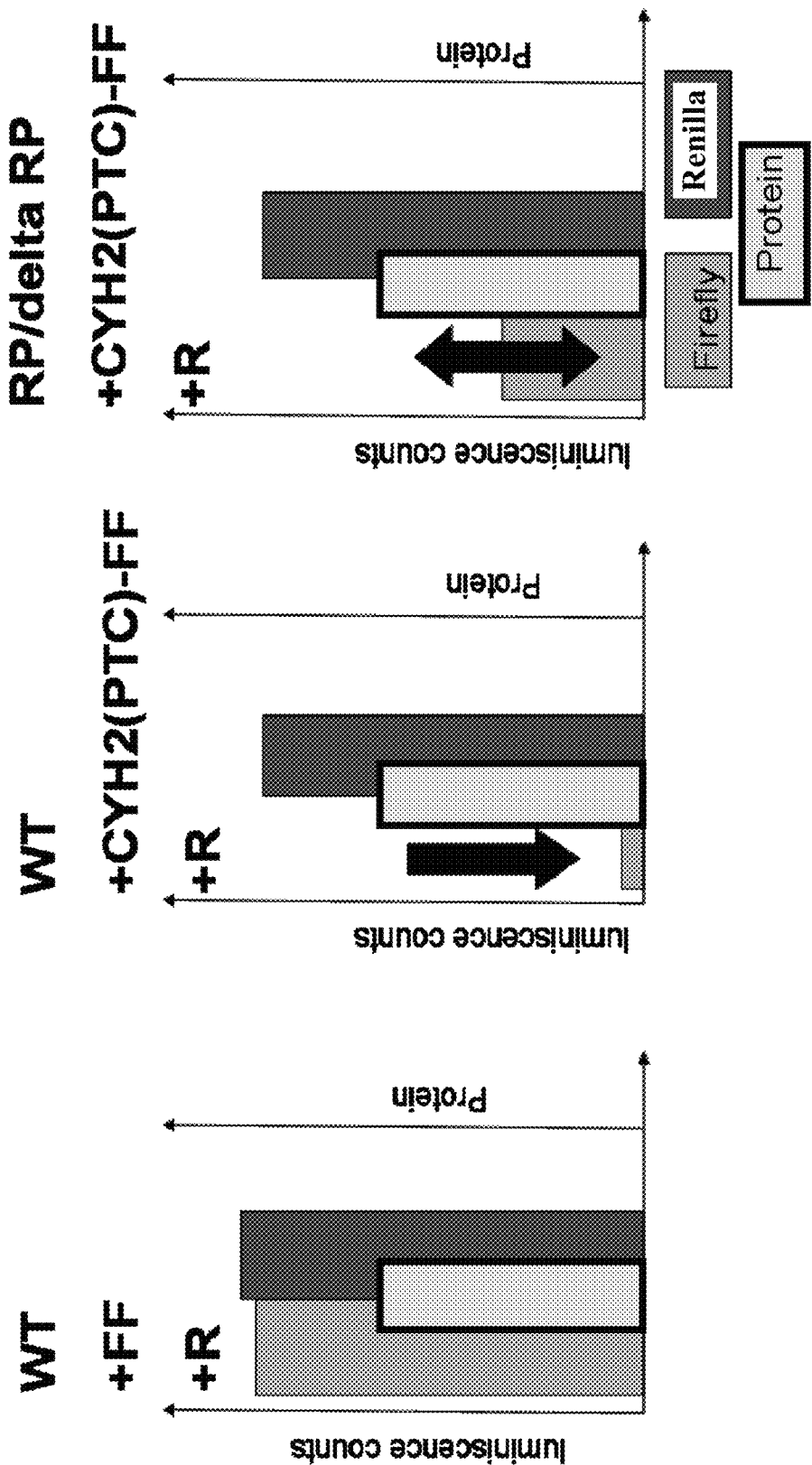
Figure 1: Comparative Dual luciferase PTC Assay System

Figure 2:
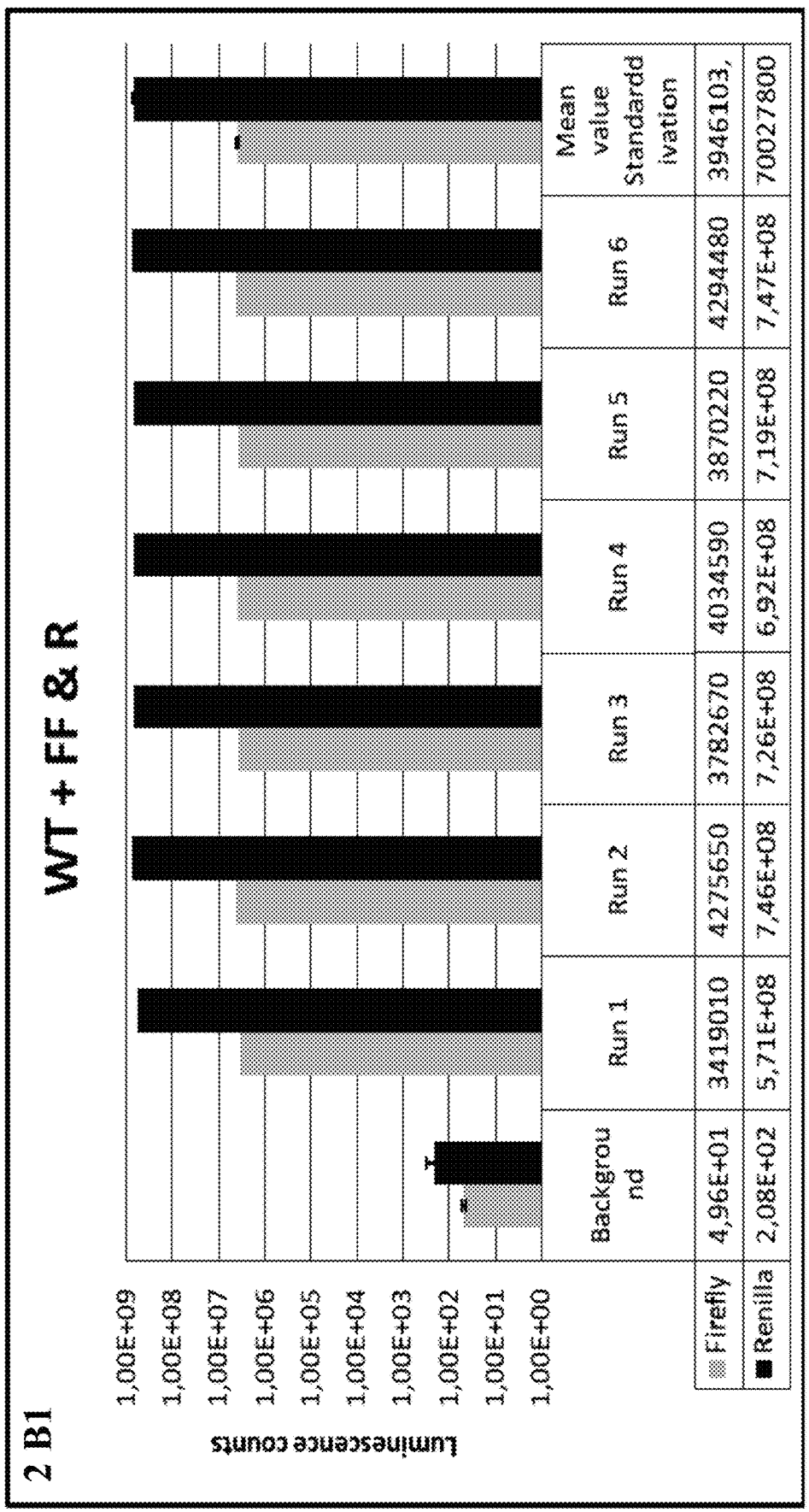
Figure 2:
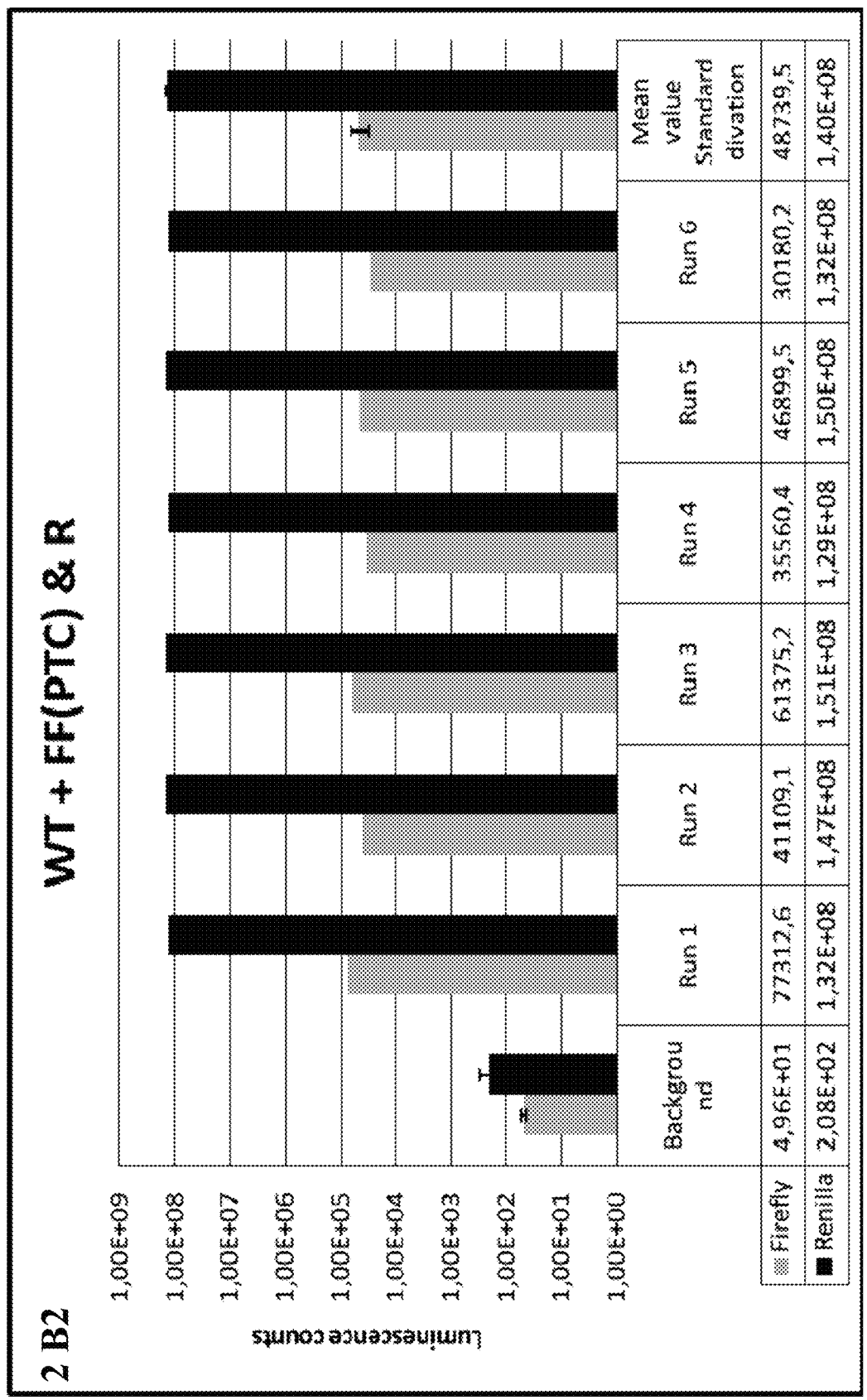
Figure 2:
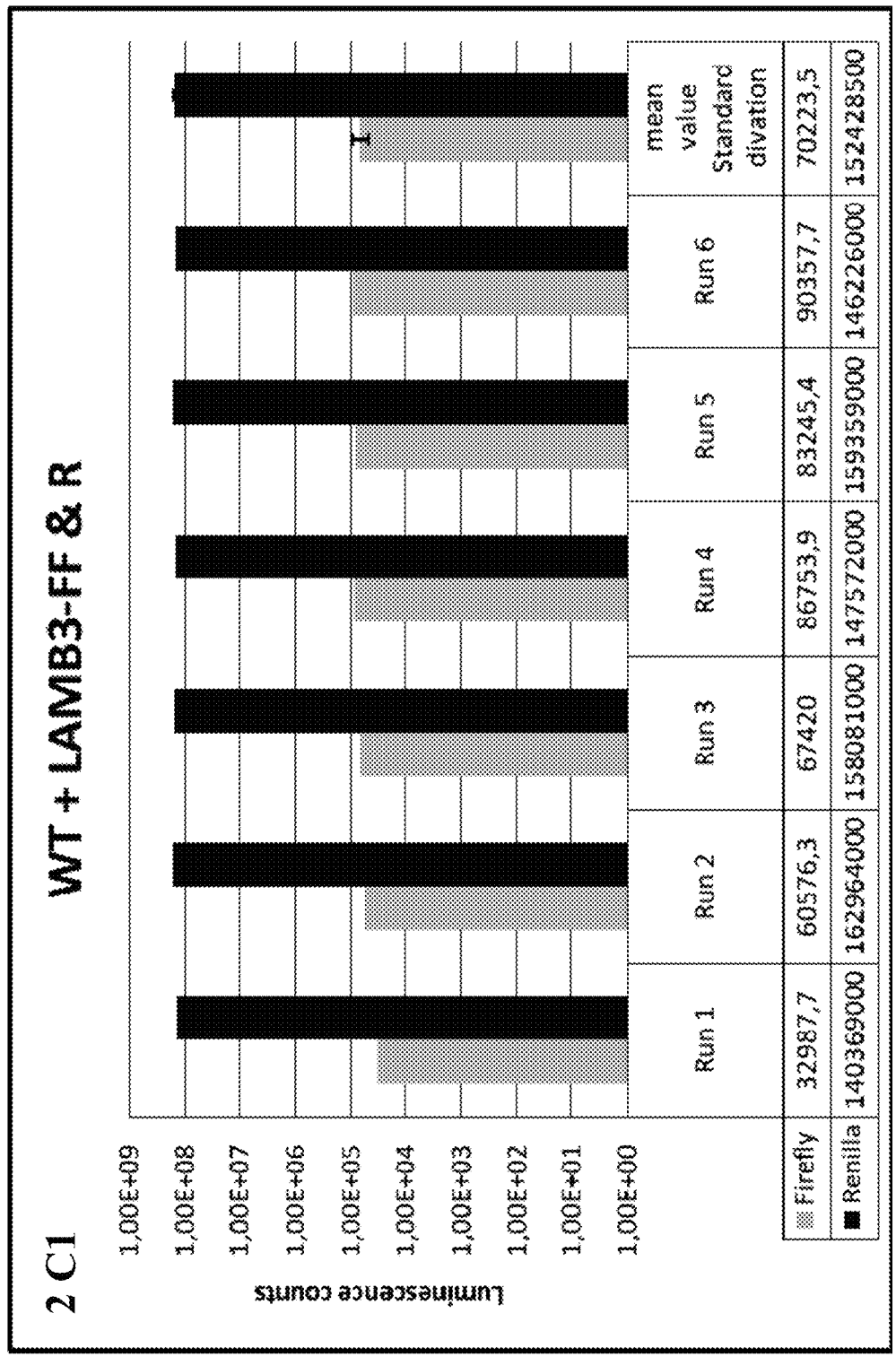
Figure 2:
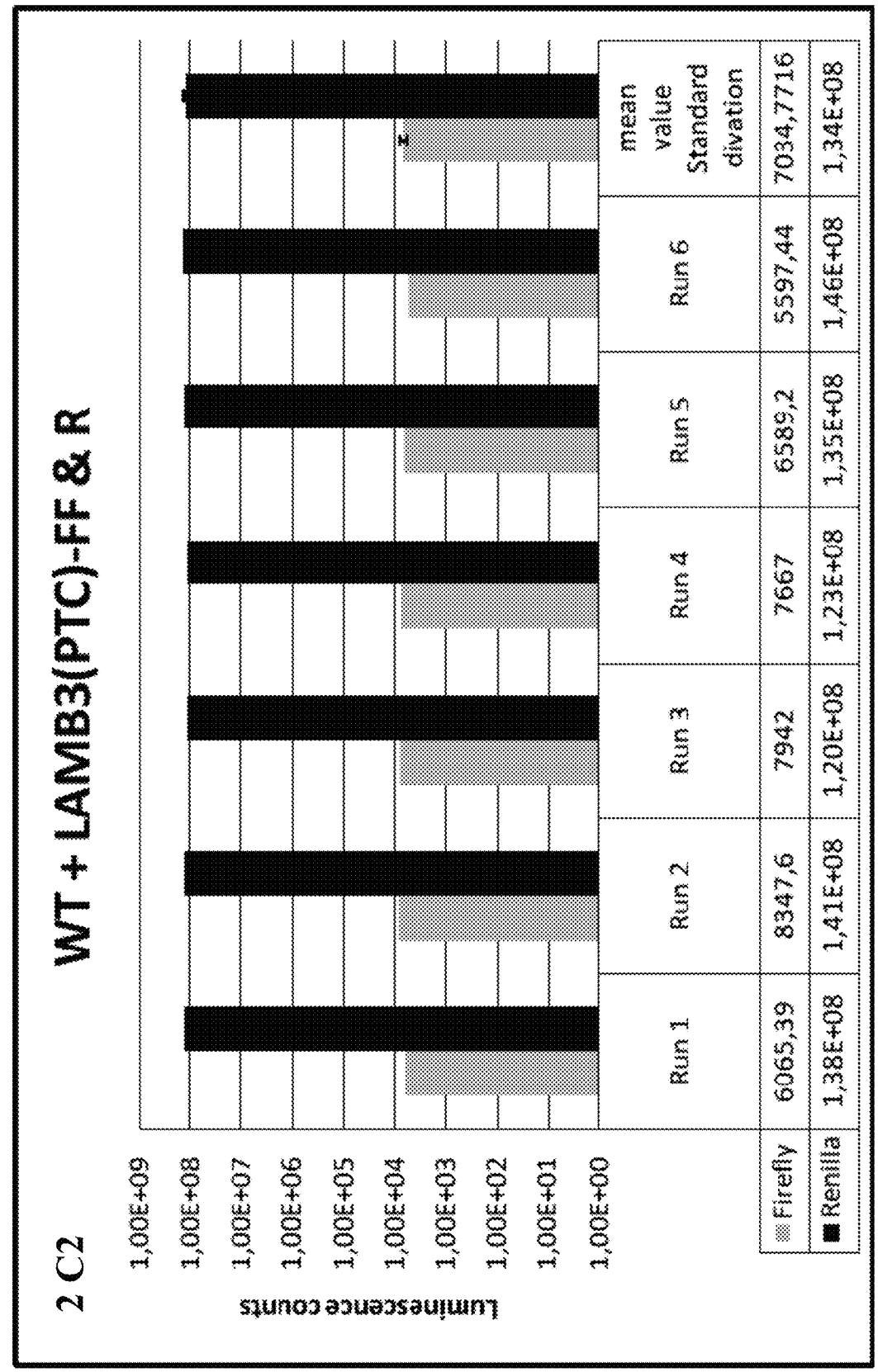

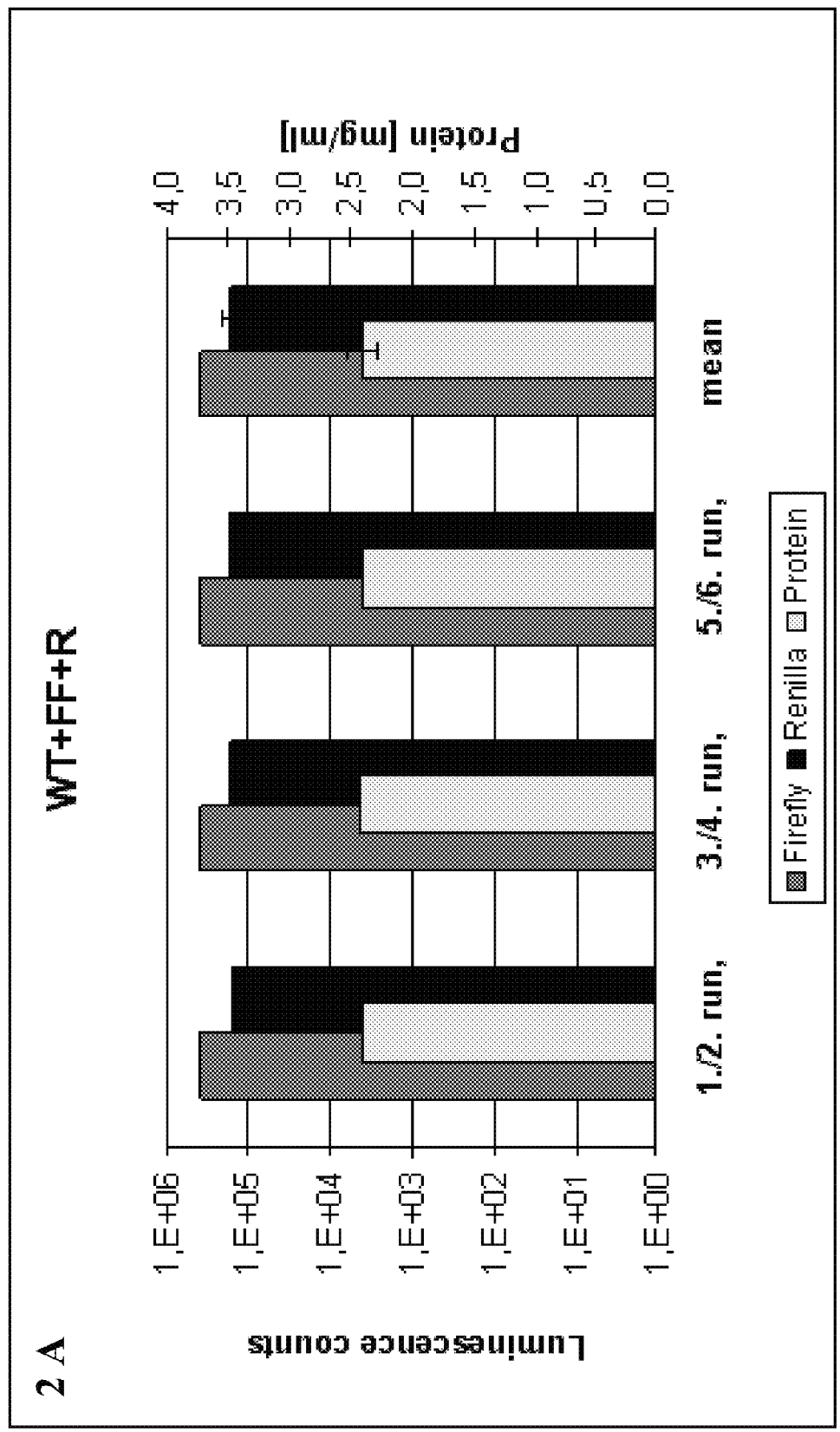
Figure 2: Optimization of the Dual Luciferase PTC reporter systems
2 A) Precision of the FF/R reporter system (2A) determined with the Anthos Lucy II luminometer 2 B) Precision of the FF/R (2B1) reporter assay determined with the Glomax luminometer (Promega)

Figure 3:
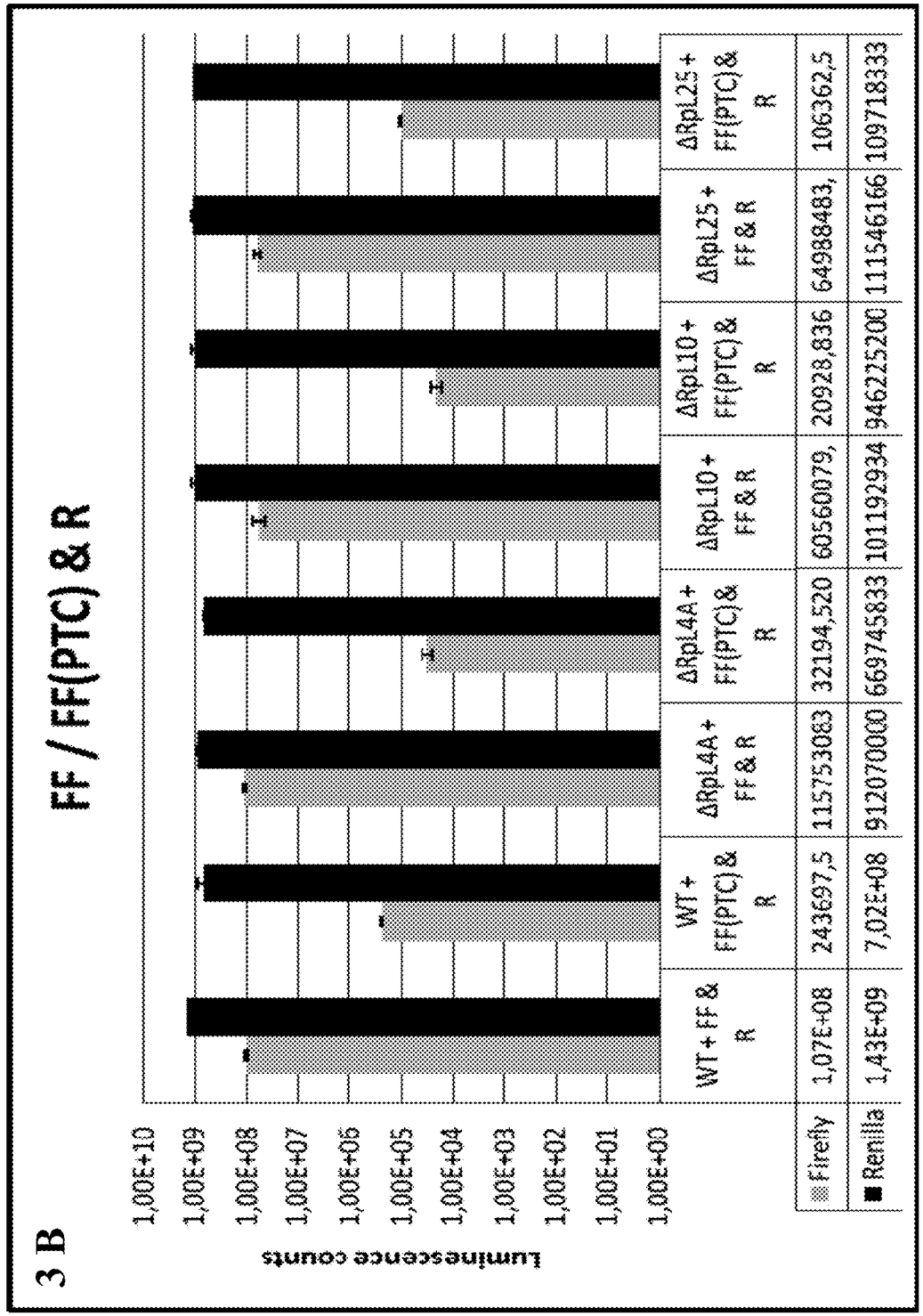

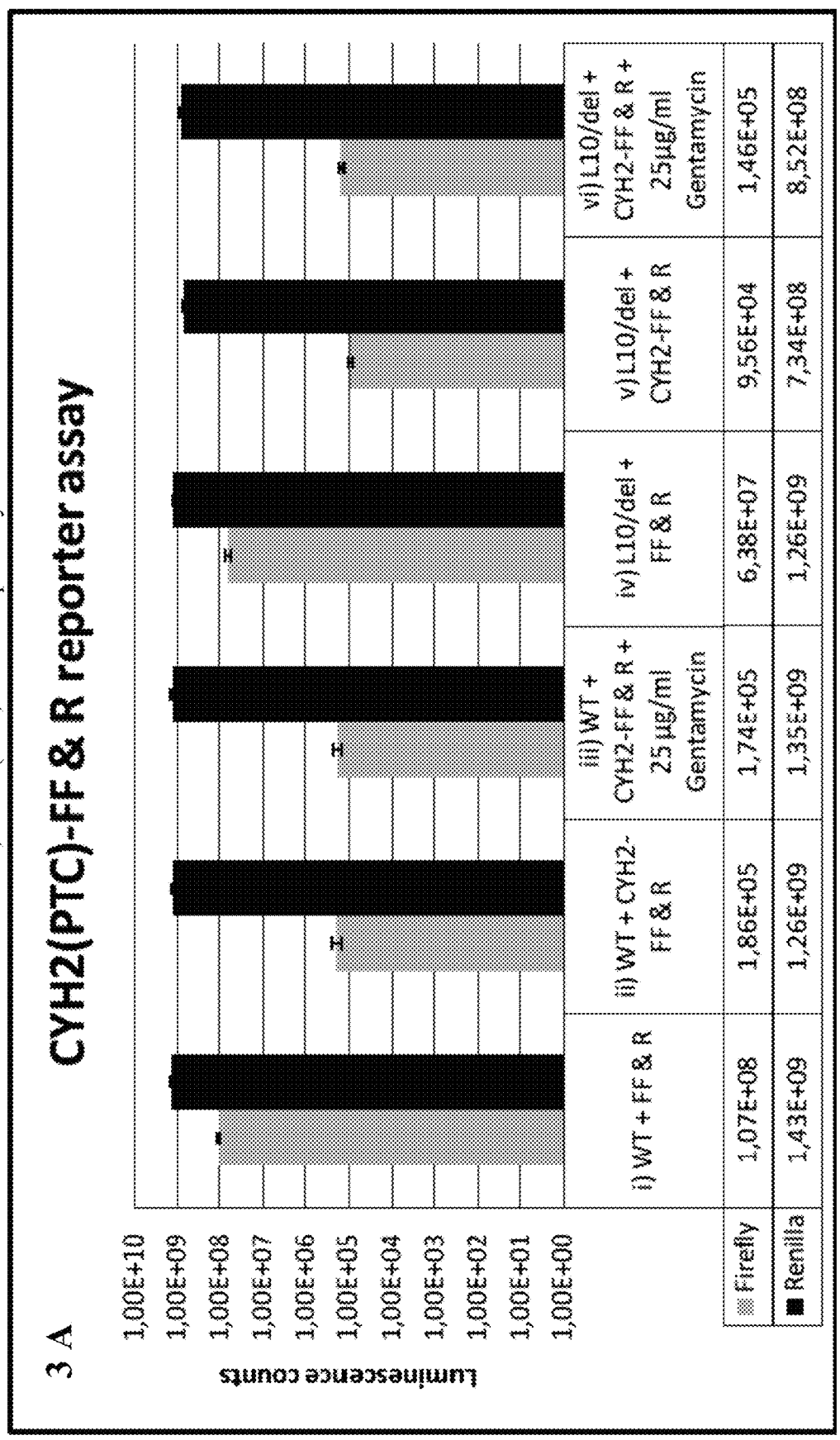
Figure 3: Gene dosage of ribosomal proteins modulates level of protein expression from PTC mRNAs (employing the Glomax luciferase signal detection system)

3 B) FF/ FF(PTC) & R reporter system

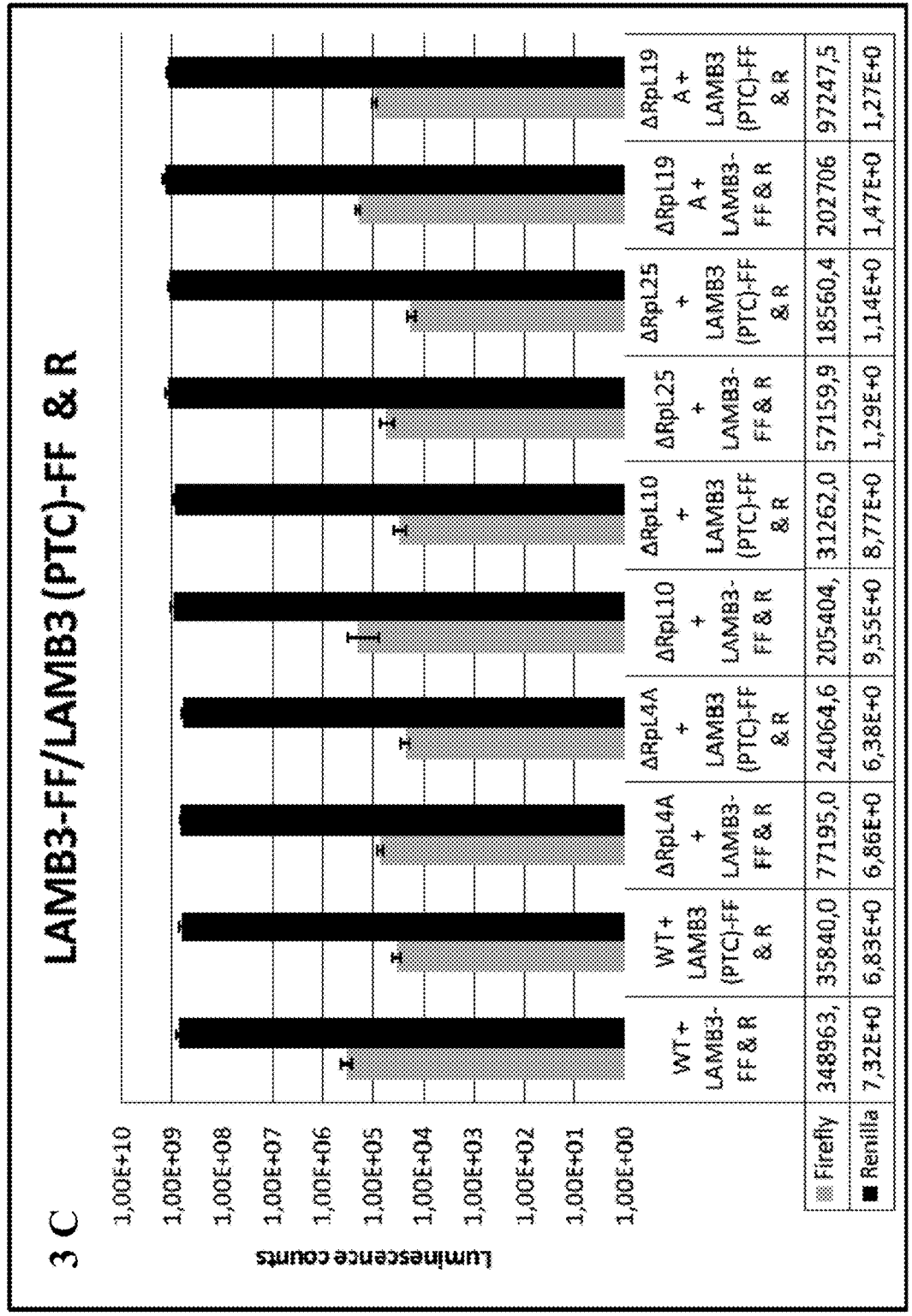

Figure 4: Comparative 2D DIGE analysis of protein expression in wild type and RPL10 gene dosage reduced cells
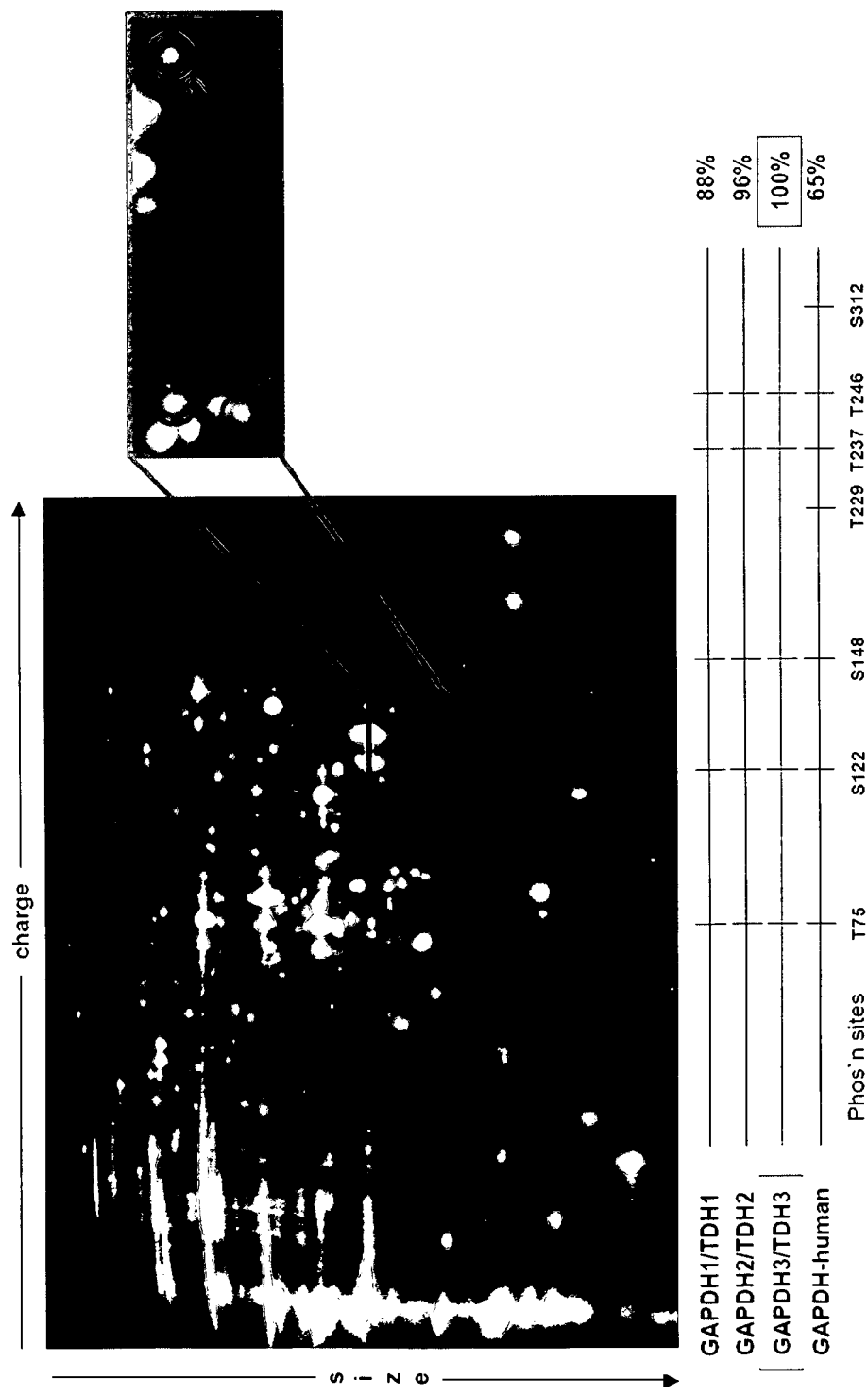

Figure 5:
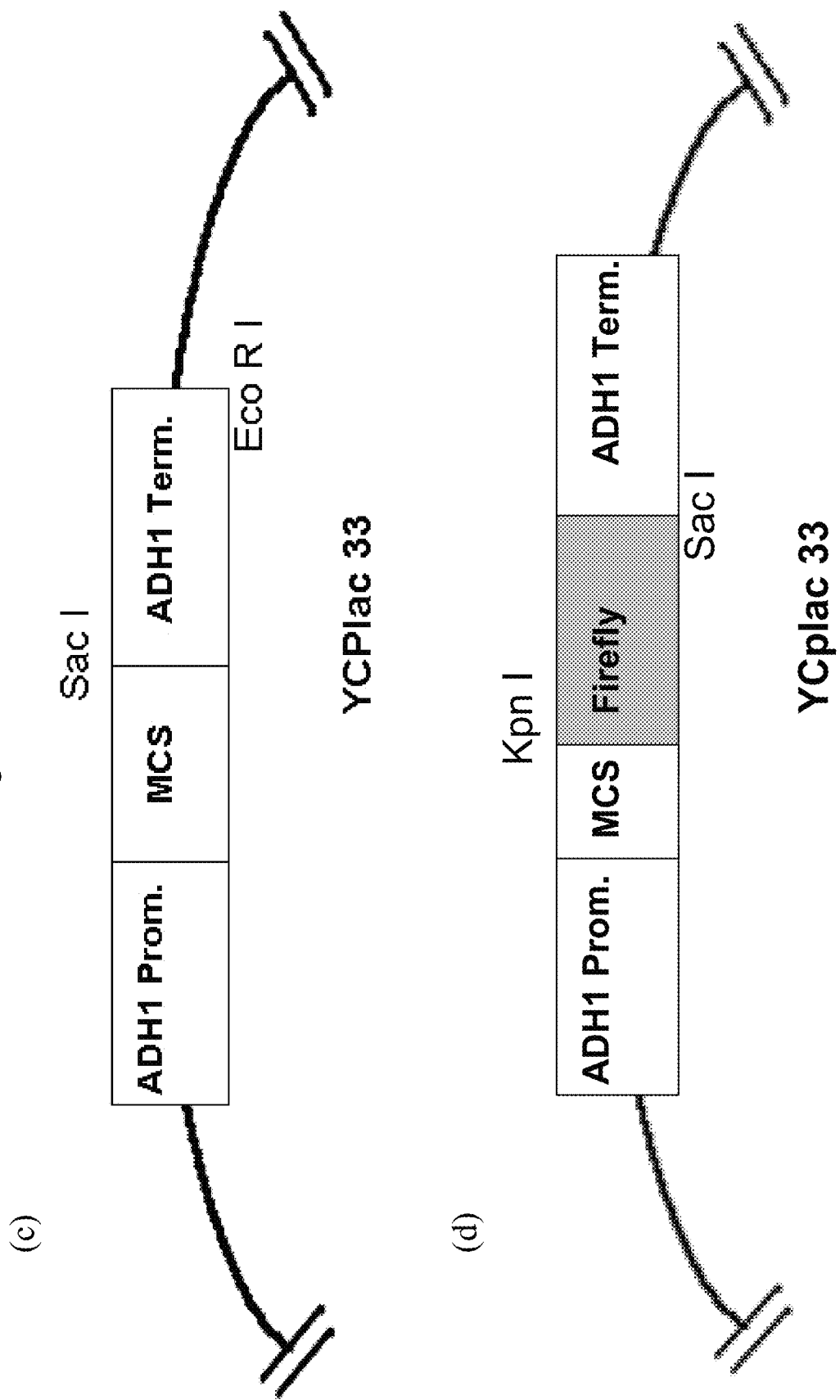
Figure 5:
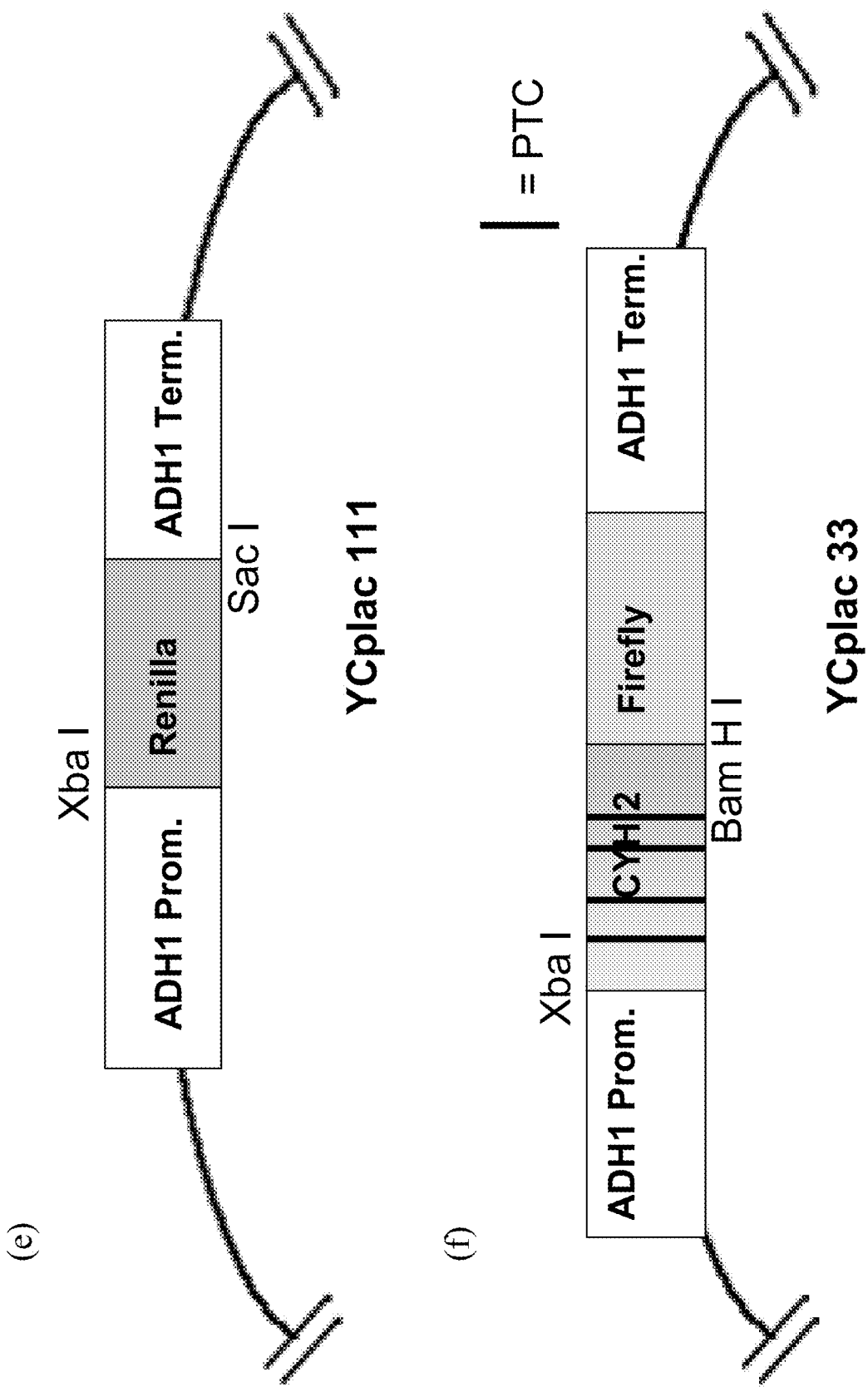
Figure 5:
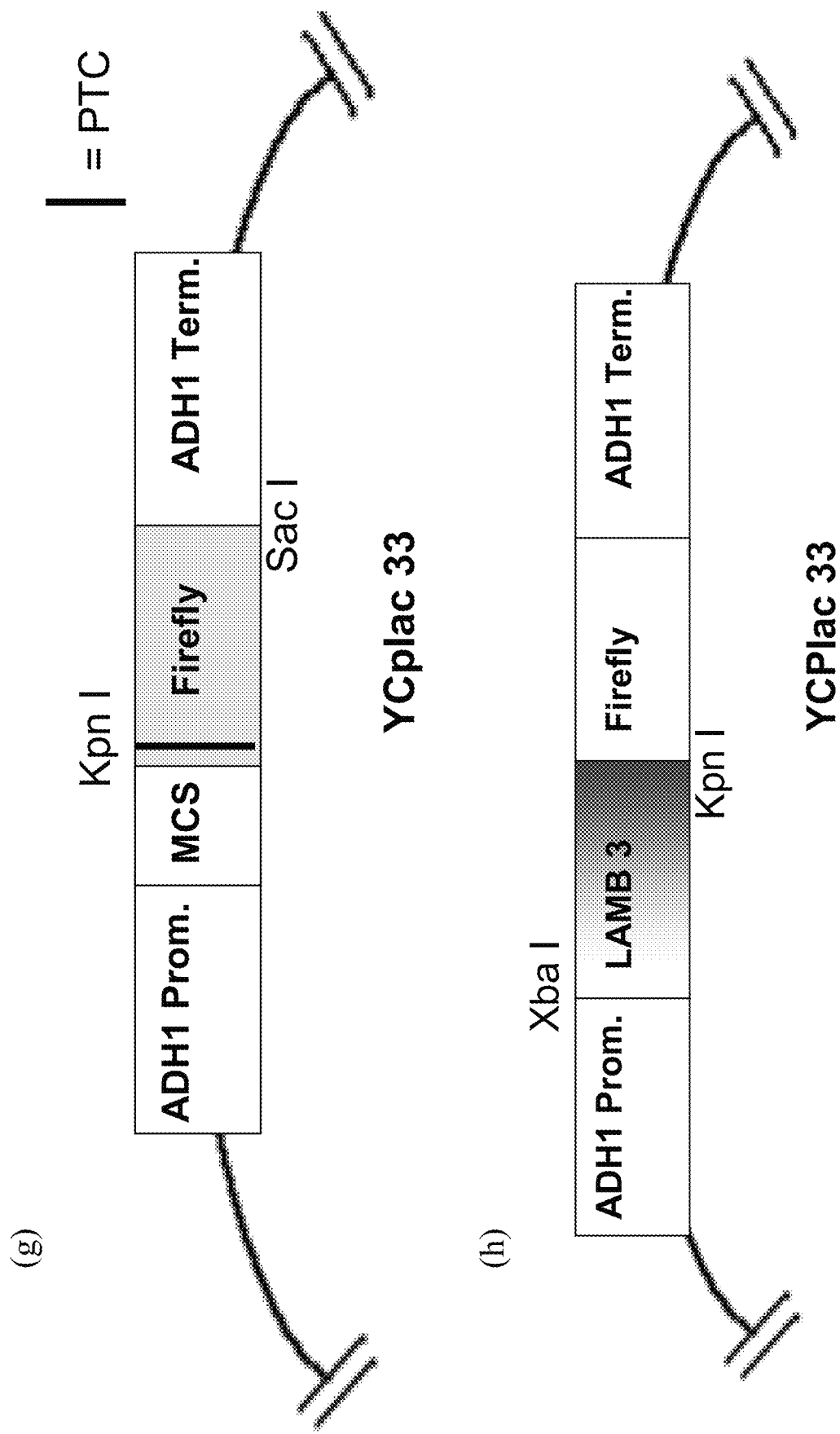
Figure 5:
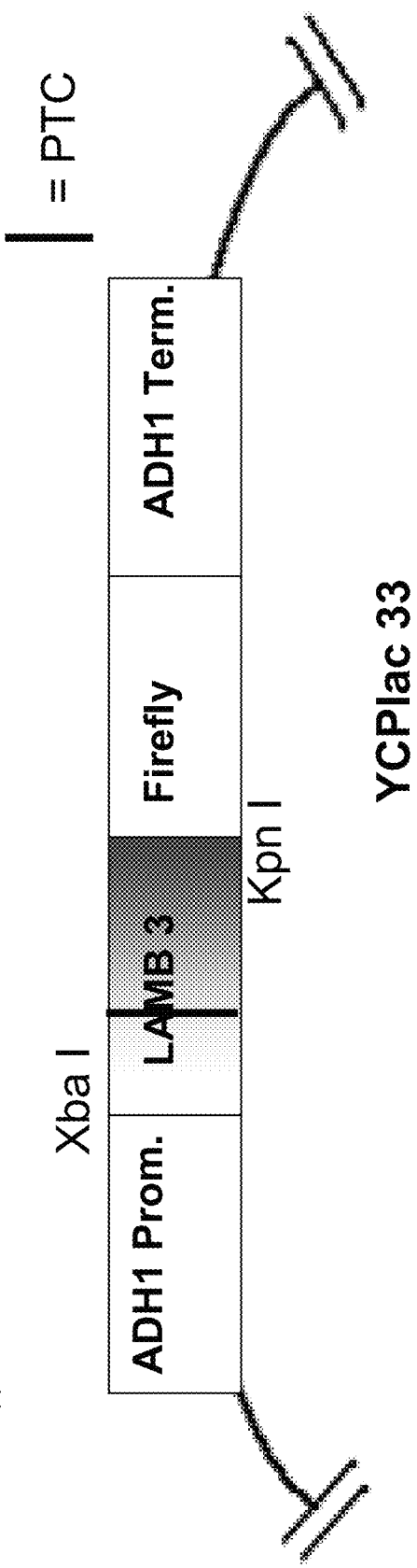

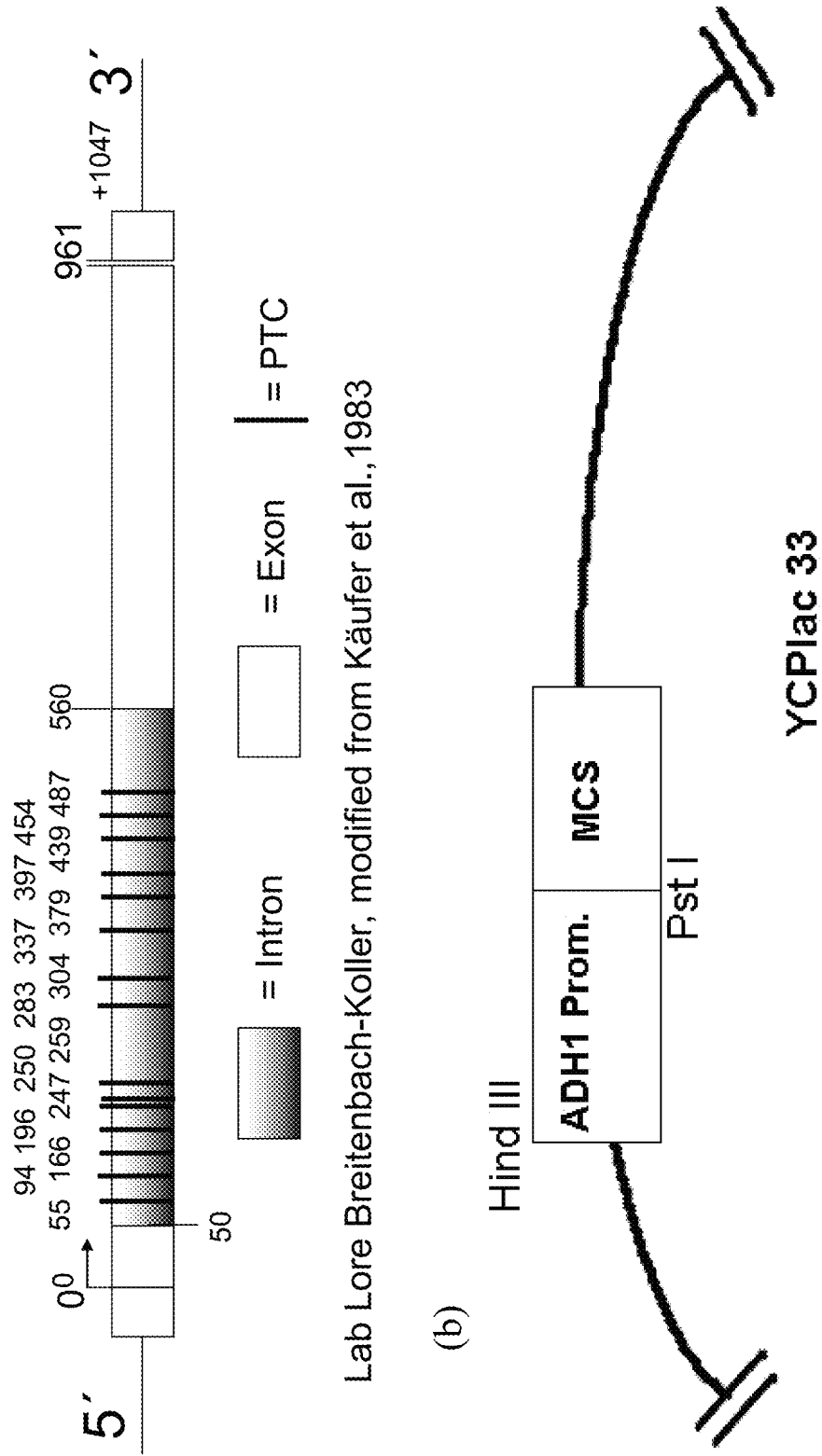
Figure 5: Reporter constructs used in the dual luciferase translation assay

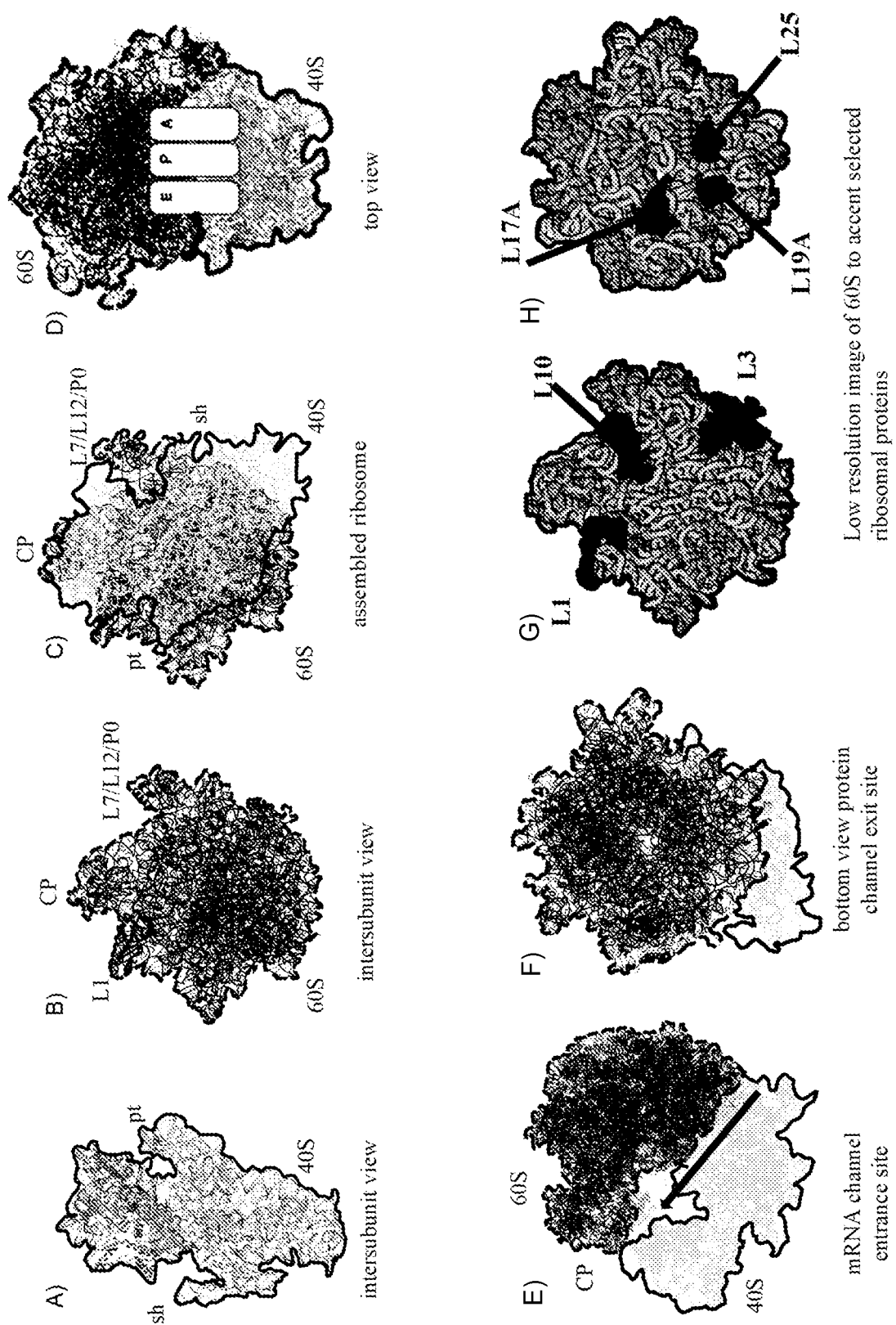
Figure 6: The yeast ribosome modified from PDB-files 1S1H/1S1I (J. Frank laboratory)

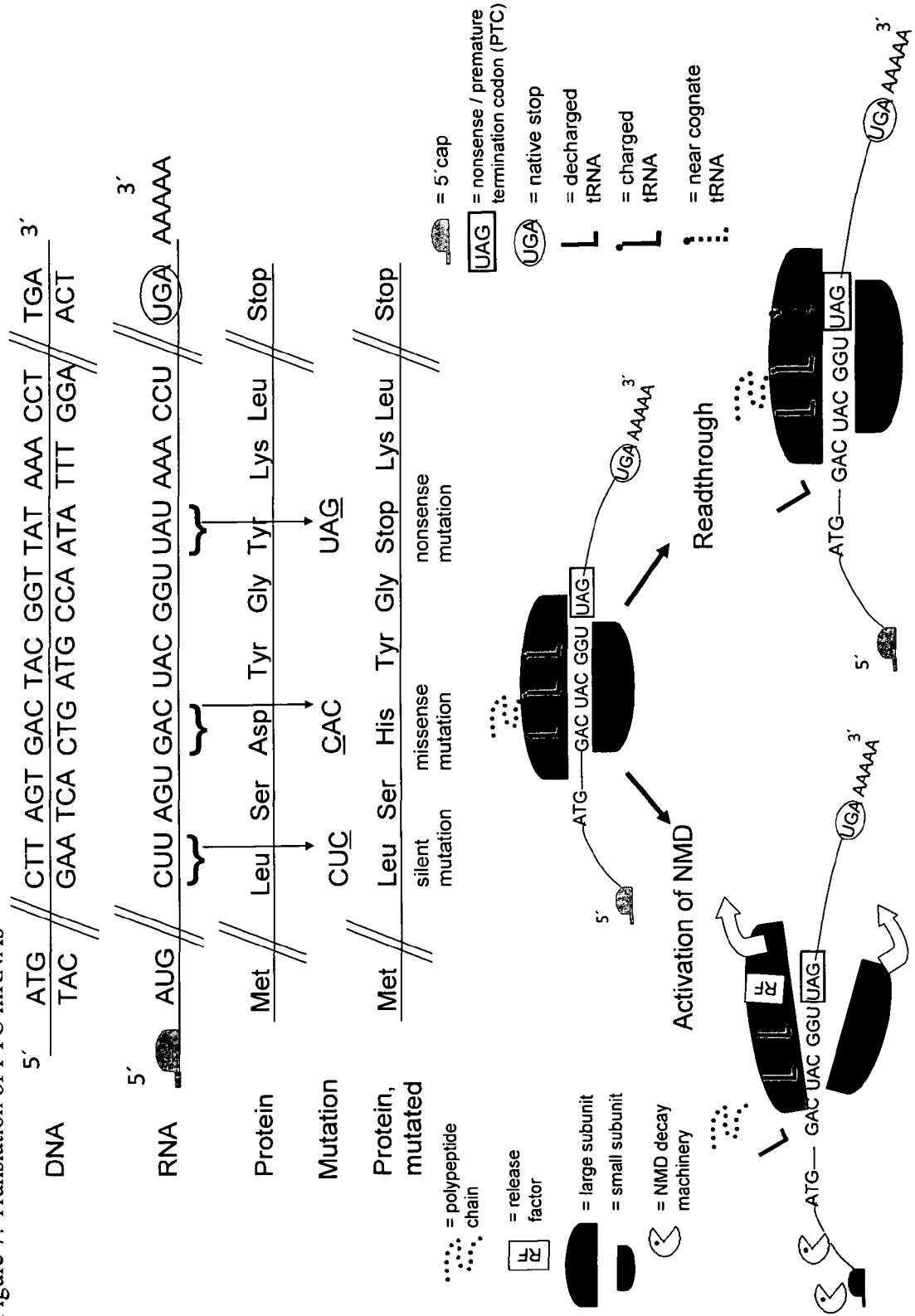

METHOD FOR IDENTIFYING INTERVENTIONS THAT CONTROL THE TRANSLATIONAL ACTIVITY OF RIBOSOMAL PROTEINS IN DIFFERENTIAL MRNA EXPRESSION

The present invention relates to systems and methods for screening compounds and/or mutant ribosomal proteins in a eukaryotic cell that increase or decrease the translation of a target gene and thereby ameliorate or revert a defective and/or undesired translation of a target gene. Disclosed are compounds and proteins as identified with the methods and systems of the invention, pharmaceutical and cosmetic compositions thereof, their uses for the preparation of a medicament, methods of treatment of a disease or condition or cosmetic condition related to the defective translation of a gene, for example genetic diseases such as Epidermolysis bullosa, as well as diagnostic measures practical for the clinical evaluation of such diseases or conditions. Also, kits are provided which comprise the identified compounds and/or proteins in addition to suitable means for performing the methods of the invention

BACKGROUND OF THE INVENTION

Current strategies for the treatment of human diseases primarily focus on systemic, chemically based strategies, strategies modulating the transcription of certain target genes, and strategies modulating the biological processing of certain target genes. Only recently, strategies modulating the translation of certain target genes are pursued.

Translation of genetic information into proteins is executed by the ribosome (FIG. 6), a molecular machine composed of two subunits, a large subunit (50S in prokaryotes, 60S in eukaryotes) and a small subunit (30S in prokaryotes, 40S in eukaryotes). In prokaryotes and eukaryotes, from yeast to man, both subunits are built from highly structured ribosomal RNA (rRNA) and ribosomal proteins (RPs), where the small subunit rRNA harbors the mRNA decoding center and the large subunit supplies the peptidyl-transferase center that catalyzes formation of the peptide bond (ribozyme). Two tunnels traverse the assembled ribosome to accept the molecules necessary for and resulting from the translation process: the mRNA channel provides the space to select and harbor aminoacylated tRNAs as specified by the codon sequence of the mRNA and the protein exit channel guides the nascent protein chain into the cellular environment. Translation factors guide the successive mechanistic events of translation initiation, elongation and termination. Translation by the ribosome is rapid and precise, where the ribosome adds up to 20 amino acids to the growing polypeptide chain per second and commits an error only every 1000 to 10.000 additions (reviewed in Aitken et al., 2010).

Within the last ten years, breakthrough crystallographic (Ban et al., 2000, Schluenzen et al., 2000, Wimberly et al., 2000, Yusupov et al, 2001) and cryoelectronmicroscopic studies (Spahn et al., 2001, Spahn et al., 2004) have provided a unprecedented fine structure analysis of prokaryotic and eukaryotic ribosomes. In order to honor this exceptional scientific work the Nobel Prize in Chemistry 2009 was awarded to Venkatraman Rhamakrishnan, Thomas A. Steitz and Ada E. Yonath for studies of the structure and function of the ribosome. Furthermore, analyses of single ribosomes, which eliminate esemble averaging, indicate that translating ribosomes can undergo large scale conformational fluctuations that can be modulated by distinct ribosomal proteins to change molecular parameters during translation of different classes of mRNAs (Aitken et al., 2010).

While the rRNA during evolution from unicellular to multicellular organisms has gained so called extension segments, the 78 ribosomal proteins found in yeast cytoplasmic ribosomes are also present in human cytoplasmic ribosomes, with conservation of sequence, structure and localization on the ribosome, although mammals have 79 ribosomal proteins in their cytoplasmic ribosome.

Although the work on the species specific control of translation initiation to discriminate between translation initiation in pathogens (bacteria and pathogenic fungi) versus mammalian cells has recently made great progress (see, for example, Brandi et al., 2008a, Brandi et al., 2008b), the understanding of the contribution of modulation of the translation process per se, i.e. the extension to differential mRNA translation within a species still lags far behind.

Taken together, these findings support the importance to search for novel modulators of protein synthesis and employment of hypothesis driven experiments to analyze the role of ribosomal proteins in differential translation of mRNA.

In many disease states, and even in cosmetic approaches, it would be extremely desirable to increase or decrease the amount of protein synthesized from a distinct, disease associated mRNA, in particular in cases where a mutation in the mRNA coding and/or regulatory region interferes with proper synthesis of the protein, leading to disease and other undesirable conditions.

At present, several drugs are known that serve this function, but they lack specificity, i.e. they increase or decrease mRNA translation of many, if not all, mRNA species, including the target mRNA (Welch et al., 2007). The drugs that modulate quantitatively mRNA translation further merely aim at the core functions of translation in order to thereby broadly prevent protein synthesis, either by targeting the decoding site of the small subunit (aminoglycosides), or interfering with two functional sites of the large subunit, either by inhibition of the rRNA based peptidyl transferase center (aminoacylated nucleoside antibiotics) or by blocking the rRNA-lined polypeptide chain exit channel (macrolides) to prevent release of the polypeptide chain. These drugs are antibiotics that selectively inhibit prokaryotic translation, with little or no effect on translation of the eukaryotic host. Interestingly, the aminoglycoside gentamycin, which abrogates prokaryotic translation by interfering with the decoding process, has less effect on this process in the case of the eukaryotic host ribosomes, but makes the eukaryotic ribosomes less efficient in the recognition of mutant premature termination codons (PTC), i.e. read-through of a PTC by a near cognate tRNA is more frequent. This is favorable in case of human disease causing PTC mRNAS, as seen in PTC associated cases of cystic fibrosis (CF). However, prolonged antibiotic treatment of CF patients has very severe side effects and much effort has been invested to develop PTC drugs which improve read-through and reduce toxicity.

The following attempts are based on approaches to generate compounds that bind the decoding region in the 3' end of the small ribosomal subunit rRNA (i.e. are RNA-target approaches) in order to modulate mRNA translation in eukaryotes, and specifically read-through of PTC mRNAs.

WO 2004/010106 describes a method for screening and identifying compounds that modulate premature translation termination and/or nonsense-mediated messenger ribonucleic acid ("mRNA") by interacting with a pre-selected target ribonucleic acid ("RNA"). In particular, the present invention relates to identifying compounds that bind to regions of the 28S ribosomal RNA ("rRNA") and analogs thereof.

EP 2007365 describes functional proteins encoded by nucleic acid sequences comprising a nonsense mutation. The publication also relates to methods for the production of functional proteins encoded by nucleic acid sequences comprising a nonsense mutation and the use of such proteins for prevention, management and/or treatment of diseases associated with a nonsense mutation(s) in a gene. The publication also describes "nonsense codon suppressor agents" that could be provided.

Similarly, WO 2004/091502 describes 1,2,4-oxadiazole benzoic acid compounds, methods of using and pharmaceutical compositions comprising an 1,2,4-oxadiazole benzoic acid derivative. Methods as described include methods of treating or preventing a disease ameliorated by modulation of premature translation termination or nonsense-mediated mRNA decay, or amelio-rating one or more symptoms associated therewith.

The above publications are based on the finding that the aminoglycoside antibiotic gentamycin shows an effect on the (general) read-through of stop ("nonsense") codons, also termed premature termination codons (see, e.g. Howard M T, Anderson C B, Fass U, Khatri S, Gesteland R F, Atkins J F, Flanigan K M. Readthrough of dystrophin stop codon mutations induced by aminogly-cosides. Ann Neurol. 2004 March; 55(3):422-6), and that compounds of this class may be of therapeutic use (Barton-Davis E R, Cordier L, Shoturma D I, Leland S E, Sweeney H L. Aminogly-coside antibiotics restore dystrophin function to skeletal muscles of mdx mice. J Clin Invest. 1999 August; 104(4):375-81). WO 2004/091502 describes compounds that try to avoid some of the drawbacks of gentamycin, such as nephrotoxicity and ototoxicity.

Despite the above progresses, a general translation misreading does generate proteins with altered function that, if not folded properly, would be prone to form toxic aggregates. Alternatively, it is possible that mistranslated proteins may act in protein complexes in a dominant way to disrupt cellular functions or may display gains-of-function that are detrimental to the cell. In addition, aminoglycosides interfere with other RNA functions including self-splicing of group I introns, HIV replication by interaction with the Rev responsive element (RRE), and hammerhead ribozyme cleavage. They are also known to disrupt plasma membranes and interfere with signal transduction involving phosphatidylinositol, possibly by inhibiting protein kinase C.

Finally, compounds such as paromomycin have been proposed as maybe effective at lower doses and may display less toxicity than compounds such as gentamycin. Direct targeting ribosomes associated with the defective mRNA has been proposed as well. For example, conjugation to antisense dystrophin oligonucleotides might provide greater specificity toward the defective dystrophin mRNA (e.g. Kaufman R J. Correction of genetic disease by making sense from nonsense. J Clin Invest. 1999 August; 104(4):367-8).

Other approaches, in particular with the aim to provide additional prokaryote-specific antibiotics for use in human disease, are known from the literature as well (for a review, see Pelletier and Peltz, Therapeutic Opportunities in Translation; in Michael B. Mathews (Ed.) Translational Control in Biology and Medicine (Cold Spring Harbor Monograph Series 48), 2007, pp 855 to 895, incorporated herein in its entirety).

In order to improve the above situation with the goal to specifically control the translation of a target mRNA ("desired" mRNA) versus an mRNA encoding for a mutated sequence ("mutated" mRNA) that leads to a undesired translation product in the cell ultimately causing an adverse condition, such as a disease phenotype, it is an object to help make available both specific functional components ("targets") in the ribosome of the cytoplasm that can be influenced or triggered in a way to specifically control the translation of the desired mRNA, as well as compounds that interact with said targets in order to influence them accordingly.

In contrast to earlier approaches aiming at the modification of translation initiation (e.g. rapamycin) or the rRNA, the present invention seeks to provide a specific control of the translation process per se, i.e. is directed at the ribosomal proteins (preferably one or several of the 78 as mentioned above) as targets. To the knowledge of the present inventors, there are no reports on the use of ribosomal proteins and modifications thereof as modifying agents in the translation of normal mRNAs or those with mutated encoding and/or regulatory regions.

Further objects and advantages will become apparent to the person of skill when reading the following more detailed description of the present invention.

In a preferred first aspect of the present invention, the invention relates to a screening system for a compound that ameliorates or reverts a defective translation of a target gene in a eukaryotic cell, comprising a recombinant eukaryotic cell a) expressing a recombinant ribosome comprising at least one deleted or mutated ribosomal protein, and b) expressing a reporter construct comprising said target gene coupled to a first reporter group to be co-expressed with said target gene, and c) optionally, expressing a second reporter construct comprising a second reporter group as an internal standard. Preferred is a screening system according to the present invention that further comprises a recombinant expression cassette, preferably an expression vector, for expressing the compound to be screened.

In this first aspect thereof, the present invention employs the finding of the present inventors that altered functions of ribosomal proteins (e.g. mutations, gene dosage effects) modulate the translation of distinct mRNAs, while not affecting the translation of the majority of the other mRNAs (Pachler et al, 2004, FIGS. 2, 3A, B and C and 4). This finding forms the basis for the methods of the present invention, and in particular allows a new and much more efficient concept in the development of a drug or composition that alter the translation of a target mRNA. As an example and proof of principle, the present invention uses a dual reporter (luciferase reporter) system, in order to identify candidates within the set of ribosomal protein modifications that modulate the translation of distinct PTC-containing and NMD-triggering (nonsense mediated decay) mRNAs (see FIG. 2).

In a CYH2-PTC reporter example (FIG. 2A), first, a modulation (increase) in the CYH2 protein expression is observed, when the CYH2 expression is compared in wild type and RPL10 gene dosage reduced strains (in genetic terms the diploid condition of the strain used here is designated RPL10/RPL10 for the wild type and RPL10/ΔRPl10 for the gene dosage reduced strain, respectively. For simplicity, in the further text, we denote a gene deletion/gene dosage reduction of a ribosomal protein X as ΔRPLX or ΔRPSX (or dRPLX and dRPSX in the Figures).

Second, a modulation in the expression of a FF protein expressed from a FF-PTC reporter was observed in gene dosage reduced yeast strains ΔRPL10, ΔRPL25, ΔRPL4A (decreased expression).

Third, a modulation of the expression of a reporter protein encoded by a LAMB3-PTC reporter was achieved in the gene dosage reduced strains ΔRPL10, ΔRPL25, ΔRPL4A (decreased) and in strain ΔRPL19A (twofold increased). LAMB3 encodes a structural component of laminin within the basement membrane of the skin. If absent or present in insufficient amounts, as in the case of a mutant PTC LAMB3, a severe blistering of the skin occurs in the disease Epidermolysis bullosa, as studied as a preferred example by the present inventors. The LAMB3PTC reporter serves as model PTC reporter in order to study a translational intervention in order to boost the full length expression of the LAMB3 protein. Thus, in sum, the present inventors provide a proof of principle that alterations in ribosomal proteins modulate the expression of distinct mRNAs, as shown here for PTC mRNAs.

In this context it is important to note that in many PTC-associated disease states or conditions a relative small increase in a protein expression from the PTC mRNA (be it by increase in PTC read-through or decrease in the PTC induced decay of the PTC mRNA, (see FIG. 7) is sufficient for a significant improvement of said disease state or condition. In other cases, in turn, it may be desirable to reduce the amount of a target protein, preferably to a minimal level.

Furthermore, the inventive model can be used to screen for compounds that ameliorate or revert a defective translation of a target gene as identified as undergoing translational control at the ribosome and analyzed accordingly. Said compounds can be used in order to develop therapeutic strategies in order to treat diseases that are related with defective ribosomal proteins and/or mRNAs.

The ribosomal proteins employed in the methods and systems of the present invention can be full-length modified proteins, or fragments with N/C-terminal and/or internal deletions. Preferably, the fragments are either N-terminal fragments or C-terminal fragments. Furthermore, the invention encompasses the use of mutated ribosomal proteins, such as proteins containing amino acid exchanges, modified amino acids, and fusion proteins. Methods for producing mutated ribosomal proteins are well known in the state of the art, and further described herein.

In a particular preferred aspect, multiple mutations within one ribosomal protein and/or several mutated ribosomal proteins, or ribosomal protein deletions are employed in combination in the methods and systems of the present invention. Promising combinations of mutant ribosomal proteins can be identified through analysis of global genetic interaction networks, as for example in yeast genetic interaction maps (Tong et al. 2004). However, it is also preferred to employ any imaginable combination of mutant ribosomal protein genes for the methods and systems of the present invention.

Depending on the kind of mutation of the at least one ribosomal protein, and, for example, the potential lethality of a deletion of said protein (Amsterdam et al. 2004), the present invention encompasses systems that are expressing both recombinant ribosomes and ribosomes as encoded by the genome of the cell. Systems that provide altered gene dosages of a chosen quantity of ribosomal proteins comprise for example a mixture of ribosomes in wild type condition and ribosomes lacking one or more ribosomal proteins. Nevertheless, further preferred is a screening system according to the present invention, wherein said eukaryotic cell exclusively expresses ribosomes that are recombinant.

Basic ribosomal function and structural assembly of its components show a high degree of conservation throughout most biological kingdoms since about 2 billion years of evolution. It is preferred that the eukaryotic cells of the present invention might be selected from a plethora of different eukaryotic model systems, preferably selected from yeast or mammalian cells, such as mouse, rat, hamster, monkey or human cells. Not only mammalian cells might be preferred, but also invertebrate cells might be used for such a screening system, including for example insect cells.

As described above, 80 proteins and 4 structural RNAs assemble to form the complex molecular machine known as the eukaryotic ribosome. In a first approximation the ribosome can be subdivided into two particles of unequal size, the 60S and 40S subunits. With respect to the herein described inventive screening system, the at least one deleted ribosomal protein necessary to form a recombinant ribosome is preferable located either in the 60S or the 40S subunit of a eukaryotic ribosome. Furthermore, to provide a screening system according to the present invention, the selected at least one deleted ribosomal protein is preferably involved in mRNA transport during elongation of translation, located in the mRNA exit tunnel or protein exit tunnel, and/or located at the intersubunit side or involved in long range interactions that change the structure of the initiating/translating ribosome. Furthermore, it is known that several ribosomal proteins are also involved in extra-ribosomal functions (Warner et al 2009). Nevertheless, the present invention is preferably directed at employing the function of a given ribosomal protein in the ribosomal context/ribosomal function in translation of a target mRNA.

In yet another embodiment of the herein described invention the inventors provide a preferred selection of candidate ribosomal proteins for the use in the screening system of the invention, comprising rPL2A, rPL2B, rPL3, rpL4A, rPL4B, rPL7A, rPL7B, rPL10, rPL11, rPL16A, rPL17A, rPL17B, rPL18A, rPL18B, Rpl19A, rPL19, rPL25, rPL29, rpL31A, rpL31B, rPL36A, rPL40A, rPS1A, rPS6A, rPS6B, rPS14A, rPS15, rPS23B, rPS25A, rPS26B, rPS29B, and rPS31. Particularly preferred is the screening system, wherein said ribosomal protein is selected from rPL2, rPL3, rPL4, rPL10, rPL11, rpL17, rPL18, rPL19, rPL25, rPS6, and rPS15.

In particular two missense mutations in human rPL10 have recently been identified in two pairs of autistic siblings, and have been functionally analyzed in the eukaryotic yeast model system in the laboratory of the inventors (Klauck et al., 2006). Thus, it is postulated that mutations in Rpl10 may contribute to autism. The two mutations that were identified were L206M and H213Q. Klauck et al. continued to show that when they substituted rPL10 with mutant human rPL10, the mutants had reduced levels of polysomes, indicating a defect in translation. These mutations fall within the C-terminal domain of rPL10 that is unique to the eukaryotic rPL10 protein. Thus, in a particular favored aspect of the invention, said mutated ribosomal protein is rPL10, and said mutation is selected from L206M and H213Q.

In the context of the present invention the terms deletion or mutation with respect to a ribosomal protein shall encompass all alterations induced with techniques known to the skilled artisan that allow for the functional alteration of a ribosomal protein compared to its wild type state, and/or the alteration of the expression level of said ribosomal protein or its respective mRNA. Enclosed are methods that interfere with appropriate protein function and/or expression at the level of genomic DNA, DNA transcription, mRNA stability and translation, protein expression and post-translational protein trafficking or protein modification. Therefore, it is yet another aspect of the invention to provide a screening system, wherein said deletion or mutation of said at least one deleted or mutated ribosomal protein is selected from a deletion or mutation causing a functional inactivation of said protein, a deletion or mutation causing the translation of a selected mRNA population, a deletion or mutation causing a run-on over a premature termination codon, a deletion or mutation causing the translation of leaderless mRNA, a deletion or mutation causing a slower or faster degradation of mRNA attached to the ribosome, and a deletion or mutation causing a gene dosage effect having an effect on the formation of the translational initiation machinery and/or the elongating ribosome and a deletion of a ribosomal protein caused by targeted RNA interference mechanisms or RNA directed DNA methylation.

RNA interference methods when used in the context of the present invention shall comprise any targeted mRNA degradation mechanism that is based on the homology of a short or long double stranded RNA molecule that, if delivered into a eukaryotic cell, directs an RNA induced silencing complex to complementary mRNA molecules, with the result of enzymatic digestion of said mRNA. Known to the person skilled in the art is the use of polynucleotides for RNA interference selected from dsRNAs, siRNAs, micro RNAs and easy RNAs. How to design efficient and specific siRNA molecules is well established in the field of RNA interference. For instance, basic principles of siRNA design can be retrieved from Reynolds et al. (Nat. Biotechnol. 2004 March; 22(3):326-30, incorporated herein in its entirety). Further enclosed are the techniques of RNA directed DNA methylation (RdDM) which provides systematic transcriptional silencing of a desired gene. Initially identified in plants, the RdDM mechanism was also recently identified to be functional in animal systems, even in mammals (reviewed in Bayne and Allshire, 2005, incorporated herein in its entirety). In RdDM, siRNA molecules initiate a for the most part unraveled process the methylation of cytosine residues in the sequence of the complementary genomic DNA. Then, the methylcytosines serve as flags for the assembly of heterochromatin around the site of DNA methylation. Thus, when applied to transcribed genetic regions (genes), or their respective five prime or three prime regulatory elements, such methylation usually results in the transcriptional silencing of that gene. miRNAs which lead to translational silencing and the use of this technology is also contemplated here.

However, the described invention preferably discloses a screening system wherein said mutation is not required in order to directly influence the binding of tRNA at the decoding site and/or wherein said mutation is not required in order to directly influence the structure of the rRNA at the peptidyltransferase center.

Mono- or polygenetic diseases and cosmetic conditions often emerge from inherited mutations or SNPs or other alterations, like those induced by the aging process, that result in mRNAs which are not translated into functional proteins. Either, the truncated or mutated protein products fail to provide their original biological function (loss-of-function) or they display dominant negative effects (gain-of-function) or even assemble into toxic aggregates of misfolded proteins which are detrimental to basic cellular functions. It is a preferred intention of the present invention to open up novel therapeutic avenues for the medical treatment of such inherited diseases and/or to find novel cosmetic approaches. Thus, in yet another preferred aspect the present invention relates to a screening system, wherein said target gene is selected from a gene encoding a protein related to a condition or disease selected from aging, CNS diseases; inflammatory diseases; neurodegenerative diseases; mental retardation diseases, for example autism, autoimmune diseases; proliferative diseases, in particular cancer; cardiovascular diseases; or pulmonary diseases; epidermolysis bullosa, amyloidosis, LINCL, hemophilia, Alzheimer's disease, atherosclerosis, giantism, dwarfism, hypothyroidism, hyperthyroidism, cystic fibrosis, obesity, Parkinson's disease, Niemann Pick's disease, cystic fibrosis, familial hypercholesterolemia, retinitis pigmentosa, Duchenne muscular dystrophy, and Marfan syndrome. In yet another preferred aspect the present invention relates to a screening system, wherein said target gene is selected from a gene encoding a protein related to a cosmetic condition selected from aging, hair loss, skin damage, sunburn (in as far as not therapeutic, wrinkles, undesired de-pigmentation, undesired pigmentation, undesired hair growth, undesired sweating, and unwanted body odor(s).

As an example, the inventors studied the LAMB3 and also the COL17A1 gene, where a nonsense mutations in the C-terminal part of the coding region results in loss of the collagen protein, important for joining cell sheets of the epidermis and dermis (Darling et al., 1997, Darling et al., 1998, Darling et al., 1999, Buchroithner et al., 2004). This leads to the blistering skin disease Epidermolysis bullosa (EB). In this and other monogenetic diseases (Cystic fibrosis, muscular dystrophy) gentamicin, a compound known to increase read through of nonsense codons, has been used to partially restore the function of proteins that are lost due to premature stop codon mutations and the resulting NMD (nonsense-mediated decay). Gentamicin is associated with severe side effects, like kidney failure and has been shown to have varying degree of efficacy in the human system, but mainly depending on the level of expression of the faulty gene. Thus it is necessary to define modulators (up-regulators) of gene expression for specific mRNAs, in the case of EB, for example COL17A1 or LAMB3. The present intervention will allow to screen for ribosomal protein gene deletions with the potential to increase translation of the faulty COL or LAMB3 mRNA. This would be proof of principle that modification of a ribosomal protein impacts on regulation of NMD associated with mutant COL XVII or LAMB3 protein and merit a hypothesis driven search for therapeutic intervention that targets the candidate ribosomal protein. Therefore it is a preferred embodiment of the inventive screening system, that said target gene is selected from COL17A1, LAMB3, and other genes involved in EB, such as Keratin 5, Keratin 14, LAMB2, LAMA3, LAMB3, LAMC2, INTB4, alpha 6, Col7, and Col1.

Furthermore, it is a preferred embodiment of the inventive screening system, that said target gene is a gene related to cosmetic conditions, such as COL1, COL3, Elastin, and Fibrillin.

In a further embodiment the present invention is then directed to a screening system as described, wherein said first and second reporter group is selected from a fluorescent protein reporter molecule, such as GFP, a bioluminescent protein reporter molecule, such as *Renilla* or firefly luciferase, internal tryptophan reporter groups, a fusion protein reporter molecule, such as hAGT, and a maltose binding protein and other reporter enzymes such as phosphatases, peroxidases, kinases, chloramphenicol transferases, and/or β-galactosidases.

Preferably, such reporter molecules are provided as recombinant constructs, wherein said first and second reporter construct is selected from an expression cassette or an expression vector, preferably a eukaryotic expression vector. It is further preferred that the expression cassette or expression vector of the present invention allows a convenient in frame insertion of the target gene upstream of the reporter gene to provide a construct wherein the target gene is co-translated with the reporter group.

In another preferred aspect of the present invention, the invention is directed at a method for identifying a ribosomal protein comprising a mutation in said protein or the gene thereof that has an effect on the translational activity of said ribosomal protein, said method comprising the steps of a) providing a recombinant eukaryotic cell expressing at least mutated modified ribosomal protein or mutated gene thereof, and b) determining the translation of a target gene in said recombinant eukaryotic cell in the presence and absence of said mutation of said ribosomal protein or mutated gene thereof.

In another preferred aspect of the present invention, the invention is directed at a method for identifying a ribosomal protein comprising a mutation in said protein or the gene thereof that has an effect on the translational activity of said ribosomal protein as above, wherein step b) is performed through expressing a reporter construct comprising said target gene coupled to a first reporter group to be co-expressed with said target gene, and further comprising c) optionally, expressing a second reporter construct comprising a second reporter group as an internal standard.

In this aspect, the present invention provides a fast, reliable and cost-effective cell (e.g. yeast) bioassay to industry, medicine and academia, to screen for a set of cells harboring ribosomal protein or ribosomal protein gene modifications (gene dosage), with the potential to favor the differential translation of a given—if applicable, human disease associated-target mRNA, while not altering the steady state translation of the residual overall mRNA pool. The candidate ribosomal protein so identified as a regulator of target mRNA translation can then be conveniently and cost effectively studied in (human) cells of a given cell culture to test its regulatory potential on protein expression of the—human, disease associated—target mRNA, and to be used for respective screening assays such as those as described herein. For this aspect of the invention, the cells and mutations that are present in the ribosomal proteins are generally the same as described for the screening system above. Mutations in the genes of the ribosomal proteins can be selected from any mutation that influences the level of the protein as present inside the cell, and are preferably mutations that cause run-on translation or nonsense mediated mRNA decay. mRNAs that contain these mutations are herein designated as "mutated mRNAs". Examples for the stability regulation of mRNA and the control of gene expression are further discussed in Cheadle C et al. (in Cheadle C, Fan J, Cho-Chung Y S, Werner T, Ray J, Do L, Gorospe M, Becker K G. Stability regulation of mRNA and the control of gene expression. Ann N Y Acad. Sci. 2005 November; 1058:196-204, incorporated by reference).

During the last years, drugs were identified that differently effect mRNA translation of distinct mRNA classes within a eukaryotic cell. A prominent example is PTC124, which targets genetic disorders caused by premature stop/termination codons (PTCs), which when untreated lead to loss or truncation of proteins resulting from unscheduled termination of protein synthesis and/or rapid degradation of the PTC containing mRNA (nonsense mediated mRNA decay, NMD). The compound PTC124 may have broad clinical applications for treatment of NMD associated diseases; in more than 2,400 genetic disorders, on average 5 to 15 percent of the patients have the disease due to a nonsense mutation (according to the University of Pennsylvania School of Medicine) These genetic disorders include cystic fibrosis (CF), Duchenne muscular dystrophy (DMD), spinal muscular atrophy, hemophilia, lysosomal storage disorders, retinitis pigmentosa, familial hypercholesterolemia and some forms of cancer. However, PTC124 targets all NMD substrates in the cell and thus also those mRNAs where a PTC is used as a regulatory element in translational control of regular gene expression (Welch E M, et al. PTC124 targets genetic disorders caused by nonsense mutations. Nature. 2007 May 3; 447(7140):87-91).

Here, in one example of the above aspect of the invention directed at the system as described in the examples below, the inventors present the functionally active cellular ribosome within a living cell as an in vivo biosensor to monitor translation of distinct mutated, and disease associated mRNAs, preferably via a dual luciferase assay.

Preferably the above method is performed with a eukaryotic cell selected from yeast or mammalian cells, such as a mouse, rat, hamster, monkey or human cell.

Yet another preferred embodiment relates to a eukaryotic cell carrying mutation(s) in a ribosomal protein, wherein said mutation(s) in said ribosomal protein produces a mutated cell having altered translational activities (Chiochetti et al. 2007). In cases where an mRNA of interest can thus be produced at higher amounts compared to the wild type (i.e. non-mutated cell), this system can be used to produce and harvest target proteins of interest. Yet another preferred embodiment thus relates to an in vitro method for producing a protein in a cell, comprising expression of said protein (preferably induced expression through factors added to the growth media etc) in a mutated cell according to the present invention as above.

Yet another preferred embodiment relates to a method for identifying a ribosomal protein comprising a mutation in said protein or the gene thereof that has an effect on the translational activity of said ribosomal protein wherein said target gene is selected from COL17A1, LAMB3, Keratin 5, Keratin 14, LAMB2, LAMA3, LAMB3, LAMC2 INTβ4, alpha 6, Col7, and Plectin.

Then, in another preferred aspect of the present invention, the invention is directed at a method for screening for a compound that ameliorates or reverts a defective translation of a target gene in a eukaryotic cell, comprising the steps of a) providing a screening system according to the present invention as described above, b) contacting said screening system with at least one compound that potentially ameliorates or reverts the defective translation of said target gene, c) measuring the expression of said target gene in the presence of said at least one compound using said first reporter group compared to the expression of said target gene in the absence of said at least one compound, d) optionally, measuring the expression of said second reporter group as an internal standard, and e) identifying at least one compound that potentially ameliorates or reverts the effects of a defective translation of a target gene by a change in the expression of said target gene in the presence of said at least one compound compared to the expression of said target gene in the absence of said at least one compound.

The present invention furthermore allows to monitor a shift in protein synthesis (quantitatively and qualitatively) for any disease-associated mutated mRNA, or mRNAs associated with cosmetic conditions as described herein, either under conditions where components of the ribosome, i.e. ribosomal proteins are modified, or after administration of a drug.

Thus the invention may be used both to identify new targets of translational control for a given target mRNA, distinct ribosomal proteins and/or to test and validate drugs that specifically modulate the protein synthesis process of a given target mRNA, preferably through interacting with the ribosomal proteins.

In addition, the invention is able to be used in molecular diagnostics, as it can be used to determine, whether or not the expression of a given mRNA is regulated at the translational level.

The mutated ribosomal proteins employed in the methods of the present invention can be full-length modified proteins, or fragments with N/C-terminal and/or internal deletions. Preferably, the fragments are either N-terminal fragments or C-terminal fragments, depending on the kind of potential interaction is expected with the N- or C-terminal fragment. Furthermore, the invention encompasses the use of mutated ribosomal proteins, such as proteins containing amino acid exchanges, modified amino acids, and fusion proteins. Methods for producing mutated ribosomal proteins are well known in the state of the art, and further described herein.

The methods described herein can be performed fully or in part in vitro in a recombinant cell, such as a human or yeast cell specifically expressing, for example, the modified ribosomal protein. Depending on the selected method, it is preferred to perform steps with screening systems using individually expressed modified ribosomal proteins, or with a system that expresses at least several ribosomal proteins, or even with a system using fully reconstituted ribosomes (including living cells). Preferred strains are ribosomal protein deletion strains derived from the EUROSCARF gene deletion set, that can be modified further, e.g. in order to used for specific screening purposes. However, also other yeast deletion collections are known to the person skilled in the art and are applicable in the screening systems described herein, for review see Scherens and Goffeau (Genome Biology 2004, 5:229, incorporated herein by reference in its entirety).

In another preferred embodiment of the method for screening according to the present invention as above further comprises identifying the target gene by it providing a screening system according to the present invention, comprising at least one ribosomal protein comprising a mutation that has an effect on the translational activity of said ribosomal protein, and ii) comparing the expression of genes of said screening system with the expression thereof in a cell that does not have said mutation in said at least one ribosomal protein, and iii) identifying said target gene as differently expressed in said screening system, compared to said cell.

In this aspect of the present invention, the invention first identifies genes that are differently expressed in the screening system according to the present invention, as reflected by different mRNA-pattern as found in cells with at least one ribosomal protein comprising a mutation that has an effect on the translational activity of said ribosomal protein versus cells without mutations. By this, target genes that are differently expressed are identified, and can be used in the screening methods of the present invention.

Preferred is the method for screening according to the present invention, further comprising grouping of target genes in accordance with said mutation in said at least one ribosomal protein. This leads to the identification of, for example, target genes specific for mutations in rPL2A, rPL2B, rPL3, rpL4A, rPL4B, rPL7A, rPL7B, rPL10, rPL11, rPL16A, rPL17A, rPL17B, rPL18A, rPL18B, Rpl19A, rPL19, rPL25, rPL29, rpL31A, rpL31B, rPL36A, rPL40A, rPS1A, rPS6A, rPS6B, rPS14A, rPS15, rPS23B, rPS25A, rPS26B, rPS29B and rPS31. Particularly preferred are target genes, specific for mutations in rPL2, rPL3, rPL4, rPL10, rPL11, rpL17, rPL18, rPL19, rPL25, rPS6, and rPS15.

Further preferred is the method for screening according to the present invention, wherein determining the expression comprises detecting and/or measuring the translation and/or the amount of mRNA of said target gene.

Yet another preferred aspect of the present invention is directed at a method for screening for a compound that ameliorates or reverts a defective translation of a target gene in a eukaryotic cell, comprising the steps of a) identifying a cell that exhibits a defective translation of said target gene, b) contacting said cell with at least one compound that potentially ameliorates or reverts the defective translation of said target gene, c) measuring the translation of said target gene in the presence of said at least one compound compared to the translation of said target gene in the absence of said at least one compound, and d) identifying at least one compound that potentially ameliorates or reverts the effects of a defective translation of a target gene by a change in the translation of said target gene in the presence of said at least one compound compared to the translation of said target gene in the absence of said at least one compound.

Preferred is a method for screening for a compound that ameliorates or reverts a defective translation of a target gene in a eukaryotic cell, wherein said compound is further identified as interacting with the proteins of the ribosomes of said cell, that is, said compound does not directly influence the binding of tRNA, and/or does not directly influence the structure of the rRNA.

Measuring of binding of the compound to the ribosomal protein can be carried out either by measuring a marker that can be attached either to the protein or to the potentially binding compound. Suitable markers are known to someone of skill in the art and comprise, for example, fluorescence or radioactive markers. The binding of the two components can, however, also be measured by the change of an electrochemical parameter of the binding compound or of the protein, e.g. a change of the redox properties of either the protein or the binding compound, upon binding or change in temperature upon binding of the protein to the binding compound. Suitable methods of detecting such changes comprise, for example, potentiometric methods or isothermic calorimetry. Further methods for detecting and/or measuring the binding of the two components to each other are known in the art and can without limitation also be used to measure the binding of the potential interacting compound to the ribosomal protein or protein fragments.

Further preferred is a method, wherein the compound as selected specifically modifies the translational activity of said ribosomal protein, that is, said compound acts merely on the function of one ribosomal protein. Nevertheless, due to the three-dimensional structure of the ribosome, the invention also encompasses compounds that interact with several associated (or to be associated) ribosomal proteins.

Particularly preferred is a method for screening for a compound according to the present invention, which further comprises analyzing the translational activity of said ribosomal protein for a specific mRNA or a specific group of mRNAs, and which further optionally comprises selecting a compound that selectively modifies the translational activity of said ribosomal protein for a specific mRNA or a specific class or group of mRNAs. Depending on the underlying condition, the specific mRNA can be selected from target gene mRNAs (non-mutated) or mutated mRNAs.

The candidate compound that is to be screened in the context of the present invention, can be any chemical substance or any mixture thereof. For example, it can be a substance of a peptide library, a library of small organic molecules, a combinatory library, a cell extract, in particular a plant cell extract, a "small molecular drug", a protein and/or a protein fragment, an antibody or an antisense oligonucleotide, preferably siRNAs, dsRNAs or miRNAs.

The term "contacting" in the present invention means any interaction between the potentially binding substance(s) with the ribosomal protein(s) and/or the recombinant cell expressing ribosomes, whereby any of the two components can be independently of each other in a liquid phase, for example in solution, or in suspension or can be bound to a solid phase, for example, in the form of an essentially planar surface or in the form of particles, pearls or the like. In a preferred embodiment, a multitude of different potentially binding candidate compound are immobilized on a solid surface like, for example, on a compound library chip, and the protein of the present invention is subsequently contacted with such a chip.

The compounds as identified in the methods of the present invention can be agonists or antagonists of the translational activity of a ribosomal protein. The activity can be modified directly or indirectly, for example through modifying the steric conformation of the protein as such, its binding to the other ribosomal proteins and/the (proper) attachment to the rRNA. Further, and most preferred, the binding and processing (e.g. "reading") of mRNA to be expressed, such as the mRNA for a target gene, or a pool of target genes, is different in the presence and absence of said compound as selected in step c) as above.

The term "antagonist" is used in the broadest sense, and includes any molecule that partially or fully blocks, inhibits, or neutralizes the translational activity of a ribosomal protein. In a similar manner, the term "agonist" is used in the broadest sense and includes any molecule that mimics/supports the translational activity of said ribosomal protein. Suitable agonist or antagonist molecules specifically include agonist or antagonist antibodies or antibody fragments, fragments or amino acid sequence variants of native ribosomal proteins, peptides, antisense oligonucleotides, small organic molecules, etc.

In another embodiment, the present invention provides oligonucleotide-based treatment regimens, in particular antisense oligonucleotide-based treatment regimens. The person of skill in the art is aware of how to develop and formulate respective oligonucleotides, such as DNA, RNA (e.g. siRNA), and/or PNA nucleotides. The compositions useful in the present invention include, without limitation, proteins, antibodies, small organic molecules, peptides, phosphopeptides, antisense and ribozyme molecules, triple helix molecules, etc. that inhibit or stimulate the function of ribosomal proteins. For example, antisense RNA and RNA molecules act to directly block the translation of mRNA by hybridizing to targeted ribosomal protein-mRNA and preventing protein translation. When antisense DNA is used, oligodeoxyribonucleotides derived from the translation initiation site, e.g., between about −10 and +10 positions of the target gene nucleotide sequence, are preferred. Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology 4, 469-471 (1994), and PCT publication No. WO 97/33551 (published Sep. 18, 1997).

These molecules can be identified by any or any combination of the screening assays discussed above and/or by any other screening technique known for those skilled in the art.

Lipofections or liposomes can also be used to deliver ribosomal related molecules into cells, such as, for example, skin cells. Where antibody fragments are used, the smallest inhibitory fragment which specifically binds to the binding domain of the target ribosomal protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., Proc. Natl. Acad. Sci. USA 90 7889-7893[1993]).

In another preferred example, said candidate compound is a ribosomal protein antisense nucleic acid or a ribosomal protein-derived polypeptide, which is optionally mutated and/or chemically modified. Preferred is a ribosomal protein-peptide that is mutated in order to function as a competitor for the translational activity of said ribosomal protein in the cell or screening model as above.

The thus selected or screened compound is then, in a preferred embodiment, modified. Said modification can take place in an additional preferred step of the methods of the invention as described herein, wherein, for example, after analyzing the translational activity of said ribosomal protein in the presence and absence of said compound as selected, said compound is further modified and analyzed again for its effect on the translational activity of said ribosomal protein. Said "round of modification(s)" can be performed for one or several times in all the methods, in order to optimize the effect of the compound, for example, in order to improve its specificity for its target protein, and/or in order to improve its specificity for the specific mRNA translation to be influenced. This method is also termed "directed evolution" since it involves a multitude of steps including modification and selection, whereby binding compounds are selected in an "evolutionary" process optimizing its capabilities with respect to a particular property, e.g. its binding activity, its ability to activate, inhibit or modulate the activity, in particular the translational activity of the ribosomal proteins.

Modification can further be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group.

In a further embodiment of the method of the present invention the interacting compound identified as outlined above, which may or may not have gone through additional rounds of modification, is admixed with suitable auxiliary substances and/or additives. Such substances comprise pharmacological acceptable substances, which increase the stability, solubility, biocompatibility, or biological half-life of the interacting compound or comprise substances or materials, which have to be included for certain routes of application like, for example, intravenous solution, sprays, liposomes, ointments, skin crème, Band-Aids or pills.

In another aspect the present invention includes ribosomal proteins identified with the screening systems and methods as described herein. Such ribosomal proteins comprise at least one mutation, deletion or other modification—chemically or genetically—which affect the translational activity of a ribosome of which said ribosomal protein forms a functional part. In particular said mutation or deletion affects the intrinsic translational activity of the ribosomal protein itself.

Particularly preferred is a compound of the invention that ameliorates or reverts a defective translation of a target gene in a eukaryotic cell which was identified with the enclosed screening systems and/or methods for screening. It is also preferred that the compound according to the present invention can be modified, for example chemically as described above.

In another aspect of the inventions, the compound that ameliorates or reverts a defective translation of a target gene in a eukaryotic cell interacts with a mutated ribosomal protein identified with a screening assay as described above.

Compounds identified by the above described screening systems can be formulated into a pharmaceutical composition, using standard techniques well known in the art.

In yet another embodiment, the invention provides a pharmaceutical preparation, comprising a compound as identified according to the present invention, and/or an active agent according to the present invention, together with a pharmaceutically acceptable carrier and/or excipient.

In one embodiment, the invention relates to the use of a compound as identified according to the present invention, or a pharmaceutical preparation thereof for the production of a medicament for the treatment of a condition or disease related to the defective translation of a target gene, preferably a condition or disease selected from aging, CNS diseases; inflammatory diseases; neurodegenerative diseases; mental retardation diseases, for example autism, autoimmune diseases; proliferative diseases, in particular cancer; cardiovascular diseases; or pulmonary diseases; epidermolysis bullosa, amyloidosis, LINCL, hemophilia, Alzheimer's disease, atherosclerosis, giantism, dwarfism, hypothyroidism, hyperthyroidism, cystic fibrosis, obesity, Parkinson's disease, Niemann Pick's disease, cystic fibrosis, familial hypercholesterolemia, retinitis pigmentosa, Duchenne muscular dystrophy, and Marfan syndrome.

Therapeutic formulations of the active compound, preferably comprising a polypeptide, antibody, oligonucleotide or compound as screened with the invention, are prepared for storage by mixing the active molecule having the desired degree of purity with optional pharmaceutically acceptable carriers, excipients or stabilizers (Remington's Pharmaceutical Sciences 16th edition, Osol, A. Ed. [1980]), e.g. in the form of lyophilized formulations or aqueous solutions.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl-dimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamin, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the treatment of a condition or disease which is related to the defective translation of a target gene, preferably those compounds with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active compound altering the defective translation of a gene may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In yet another embodiment, the invention provides a cosmetic preparation, comprising a compound as identified according to the present invention, and/or an cosmetic active agent according to the present invention, together with a cosmetically acceptable carrier and/or excipient.

In one embodiment, the invention relates to the use of a compound as identified according to the present invention, or a cosmetic preparation thereof for the cosmetic treatment of a cosmetic condition related to the defective translation of a target gene, preferably a condition selected from aging, hair loss, skin damage, sunburn (in as far as not therapeutic, wrinkles, undesired de-pigmentation, undesired pigmentation, undesired hair growth, undesired sweating, and unwanted body odor(s). Another aspect relates to a method of treating a cosmetic condition related to the defective translation of a target gene, preferably a condition selected from aging, hair loss, skin damage, sunburn (in as far as not therapeutic, wrinkles, undesired de-pigmentation, undesired pigmentation, undesired hair growth, undesired sweating, and unwanted body odor(s), comprising administering a cosmetic preparation according to the present invention to a patient in need thereof.

Similar to the therapeutic formulations as discussed above, the cosmetically active compound, preferably comprising a polypeptide, antibody, oligonucleotide, small organic molecule or compound as screened with the invention, are prepared for storage by mixing the active molecule having the desired degree of purity with optional pharmaceutically acceptable carriers, excipients or stabilizers (Remington's Pharmaceutical Sciences 16th edition, Osol, A. Ed. [1980]), e.g. in the form of lyophilized formulations or aqueous solutions.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl-dimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamin, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The cosmetic formulation herein may also contain more than one active compound as necessary for the treatment of a cosmetic condition which is related to the defective translation of a target gene, preferably those compounds with complementary activities that do not adversely affect each other. Such molecules are suitably present in combination in amounts that are effective for the purpose intended.

The active compound altering the defective translation of a gene may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Preferred cosmetic formulations are for external use, such as crèmes, lotions, gels, and ointments.

A further aspect of the present invention is directed to a kit for identifying a compound that ameliorates or reverts a defective translation of a target gene, comprising a) a recombinant eukaryotic cell according to the methods and/or systems of the invention, b) a receptor plasmid for the in frame insertion of a target mRNA upstream of a first reporter group and/or a control plasmid harboring a second control reporter, c) means for performing said first reporter assay, d) optionally, means for performing said second reporter assay and e) instructions for practicing a method of screening for a compound that ameliorates or reverts a defective translation of a target gene.

In yet another aspect, a kit according to the invention further comprises e) a collection of compounds that potentially ameliorate or revert a defective translation of said target gene.

In a further aspect a kit of the present invention comprises one or more containers and an instruction. Suitable containers include, for example, bottles, vials, multi-well plates and test tubes. The containers may be formed from a variety of materials such as glass or plastic. The containers may hold one or more eukaryotic cells comprising a recombinant ribosome useful for the screening system or for methods of the present invention. Preferably, such a eukaryotic cell is a yeast mutant cell, for example selected from a yeast ribosomal mutant strain collection as described above. The kit further includes a receptor plasmid for the in frame insertion of a target mRNA upstream of the reporter construct and a control plasmid harboring the second control reporter. Preferably the first reporter construct is a firefly luciferase and the control reporter a *Renilla* luciferase. Additionally, containers may hold means for performing the first and second reporter assays needed to quantify the translation of a target gene. Preferably such means include, but are not limited to, substrates and reaction buffers required to induce an enzymatic reaction that produces a quantitative signal that correlates to the translation of the first and/or second reporter group. Preferably, a kit of the present invention further comprises containers which hold a collection of compounds that potentially ameliorate or revert a defective translation of said target gene.

Yet another aspect of the invention then relates to the use of a compound, identified with a screening system or method according to the present invention, for the production of a medicament or cosmetic to treat a disease or condition related to a defective translation of a gene, wherein said defective translation of a gene is ameliorated or reverted by said compound. Preferably, said compound functionally interacts with at least one mutated ribosomal protein identified by the herein described methods and/or systems of the invention.

In still another embodiment the invention relates to a method for diagnosing a disease or cosmetic condition related to the defective translation of a target gene, comprising the steps of a) obtaining a DNA sample from a patient, b) amplifying said target gene from said DNA sample, and c) using said amplified target gene in a method for screening for a compound that ameliorates or reverts a defective translation of said amplified target gene in a eukaryotic cell, d) and/or using said amplified target gene in a method for identifying a ribosomal protein comprising a mutation that has an effect on the translational activity of said ribosomal protein.

In still another embodiment the invention relates to a compound that mimics the translational activity of a ribosomal protein comprising a mutation that has an effect on the translational activity of said ribosomal protein as identified using a screening system according to the present invention as above.

This invention further embodies a method of treatment or prevention of a disease or condition that is related to a defective translation of a gene in a human in need thereof, comprising administering to said human a therapeutically or prophylactically or cosmetically effective amount of a compound identified with a method or system of the invention, or a pharmaceutical composition according to the present invention. It is preferred that said disease or condition is selected from a group comprising aging, CNS diseases; inflammatory diseases; neurodegenerative diseases; mental retardation diseases, for example autism, autoimmune diseases; proliferative diseases, in particular cancer; cardiovascular diseases; or pulmonary diseases; epidermolysis bullosa, amyloidosis, LINCL, hemophilia, Alzheimer's disease, atherosclerosis, giantism, dwarfism, hypothyroidism, hyperthyroidism, cystic fibrosis, obesity, Parkinson's disease, Niemann Pick's disease, cystic fibrosis, familial hypercholesterolemia, retinitis pigmentosa, Duchenne muscular dystrophy, and Marfan syndrome or from a cosmetic condition related to the defective translation of a target gene, preferably a condition selected from aging, hair loss, skin damage, sunburn (in as far as not therapeutic, wrinkles, undesired de-pigmentation, undesired pigmentation, undesired hair growth, undesired sweating, and unwanted body odor(s).

"Treatment" as used herein refers to both therapeutic and cosmetic treatment and prophylactic or preventative measures, wherein the object is to prevent or slow down (lessen) the targeted pathologic condition or disorder, for example Epidermolysis bullosa. Those in need of treatment include those already with the disorder as well as those prone to have the disorder or those in whom the disorder is to be prevented.

In another embodiment of the invention, a kit useful for the diagnosis or treatment of the disorders described herein is provided.

In yet another embodiment, the present invention concerns a diagnostic kit for Epidermolysis bullosa, comprising: a container comprising materials for performing a diagnostic method according to the present invention, together with suitable carriers and instructions for use.

In sum, the present invention offers to industry, medicine and academia a fast and affordable in vivo assay to test the contribution of ribosomal protein gene deletions and/or mutations to modulation of translation of a protein encoded by a mRNA with mutations in the coding and/or regulatory region.

The invention shall now be further described in the following examples with reference to the accompanying Appendices and Figures, nevertheless, without being limited thereto. For the purposes of the present invention, all references as cited herein are incorporated by reference in their entireties.

FIG. 1: Schematic representation of comparative dual luciferase PTC assay as employed here. Firefly (FF) and Renilla (R) in wild type (WT) yeast cells are compared with luminescence counts of a PTC-FF reporter (e.g. the CYH2-PTC-FF reporter) in wild type yeast cells, wherein a PTC reduces the FF protein and thus luminescence. Monitoring expression of the FF-CYH2-PTC in a given RP/delta RP strain reveals whether CYH2 reporter protein has an increased, decreased or unaltered expression level when compared to the WT.

FIG. 2: Optimization of the dual Luciferase PTC reporter systems. These figures show that the experiments according to the present invention are highly reproducible. FIG. 2A: Three individual Firefly and Renilla luciferase measurements are shown in the first three columns, the median values and the standard deviation are shown in the fourth column. The optimized assay conditions were then used for the studies with the CYH-PTC-FF/REN reporter system (FIG. 3A). FIGS. 2B1 and 2B2, and FIGS. 2C1 and 2C2, respectively, show the precision, mean value and standard deviation of the assay system as established in wild type cells and subsequently used in the analysis of the FF, FF(PTC), the LAMB/FF, and the LAMB3(PTC)/FF reporter in the screening of the candidate ribosomal protein deletion strain (FIGS. 3B and 3C).

FIG. 3: Gene dosage of ribosomal proteins modulates level of protein expression from PTC mRNAs. FIG. 3A shows the exemplary CYH2-PTC reporter system with the Firefly and Renilla (R) reporters. The columns show from left to right: i) the wild type control with both luciferases, Firefly and Renilla; ii) the CYH2-PTC Firefly and Renilla system, when the CYH2 PTC reporter is in front of the firefly luciferase, the firefly signal is reduced, as expected from a PTC signal; iii) the CYH2-PTC Firefly and Renilla system, when gentamycin—an inducer of ribosomal read through—is added, the signal increases; iv) the CYH2Firefly/Renilla system of i) in the RPL10 deletion strain, RPL10/ΔRPL10 without CHY2 is identical to the WT (i.e. translation of the basic firefly and Renilla reporters identical, an indication that general translation is not altered); v) the CYH2-PTC Firefly reporter is considerably less reduced in RPL10/ΔRPL10 i.e. the reduction in RPL10 favours expression of the PTC mRNA; and vi) The effect of gentamycin is not strong or not present at all in a strain with reduced RPL10 availability. In FIG. 3B, a modulation of the expression of the FF/FF(PTC) reporter in selected ribosomal protein deletion strains is shown. In FIG. 3C, a modulation of expression of the LAMB3-FF/LAMB3(PTC)-FF reporter in selected ribosomal protein deletion strains is shown.

FIG. 4: Comparative 2D DIGE analysis of protein expression in wild type and RPL10 gene dosage reduced cells. The comparative 2D gel analysis shows that a gene dosage reduction of RPL10 is associated with differential increase in isoforms of GAPDH3 expression, a eukaryotic regulator of apoptosis and oxidative stress.

FIG. 5: Reporter constructs used in the dual luciferase translation assay. Schematic overviews of the genetic constructs as used in the examples are shown, namely
  a) the CYH2-PTC-reporter;
  b) pLBK 160, parent vector YCPlac33 with ADH1 promoter and MCS;
  c) pLBK 161, parent vector YCPlac33 with ADH1 promoter, MCS and ADH1 terminator;
  d) pLBK 162, pLBK161 with wild type Firefly luciferase sequence;
  e) pLBK 164, parent vector YCPlac111 with ADH1 promoter, Renilla luciferase and ADH1 terminator;
  f) pLBK 165, pLBK 162 with CYH2-PTC reporter;
  g) pLBK 167, pLBK 162 with PTC mutation in FF;
  h) pLBK 168, pLBK 162 with LAMB3; and
  i) pLBK 169, pLBK 162 with LAMB3(PTC).

FIGS. 6A-6G show the yeast ribosome modified from PDB files 1 S1H/1S1J (J. Frank Laboratory). For a better understanding of the structural basis of the invention presented here, it is helpful to visualize the ribosomal subunits and the assembled ribosome as shown in FIGS. 6A, 6B, and 6C. Ribosomal landmark structures of the large subunit (L1 stalk, central protuberance CP and L7/12/P0 stalk) and the small subunit (sh, shoulder and pt, platform) are indicated. The large and small ribosomal subunit, each built from a core of ribosomal RNA (rRNA) to which ribosomal proteins (RPs) are attached, are joined to form an mRNA tunnel through which the mRNA is threaded during protein synthesis (FIG. 6E). Below and above the mRNA tunnel, the bulk mass of the ribosomal subunits is joined by flexible inter-subunit bridges. Superimposed on the mRNA tunnel are three pockets, called A-Site, P-Site and E-Site (FIG. 6D), the walls of which are jointly formed by inter-subunit structures of the small and large subunit. On their way through the ribosome during protein synthesis the A-Site accommodates aminoacylated tRNA, the P-Site peptidyl tRNA, and the E-Site empty tRNA, respectively. The mRNA decoding center is provided by the small subunit rRNA part of the A-Site ("the Ramakrishnan bases") and the peptidyl-transferase center is formed by the rRNA core of the large subunit. From the peptidyltransferase center, a protein exit tunnel runs through the large subunit, accepts the nascent polypeptide chain and guides the nascent protein into the cellular environment (FIG. 6F). In FIGS. 6G and 6H, selected ribosomal proteins are indicated.

FIG. 7 schematically depicts the translation of PTC mRNAs. Premature stop codons (PTCs) arise from mutational events on the DNA, are transcribed into "faulty" stop codons on mRNAs, and subject a PTC mRNA to two possible pathways upon recognition by the ribosome during translation a) nonsense mediated mRNA decay (NMD) orb) read-through of near cognate tRNAs. NMD leads to degradation of the PTCmRNA and production of a truncated protein; read-through produces a full length protein by incorporation of near cognate aminoacylated tRNA.

EXAMPLES

The present invention as an example embodiment thereof uses wild type yeast laboratory strains and derivatives thereof, wherein one of the 137 yeast ribosomal protein genes (single and duplicated ribosomal protein genes encode for the 78 or 79 ribosomal proteins in yeast and mammalian cells, respectively) has been deleted. These strains are transformed with two luciferase reporter plasmids, both under the control of the yeast ADH1 promoter and ADH1 terminator sequence tracts. One plasmid harbors a firefly luciferase reporter gene, upstream of which a multiple cloning site can receive any target mRNA coding sequence. The second plasmid harbors a *Renilla* luciferase reporter gene. The invention provides the set of ribosomal gene deletion strains that increase, decrease or do not alter the synthesis of both luciferases. Of special interest in the analysis of target mRNAs harboring mutant sequence tracts in their coding regions are the deletion strains that do not alter protein synthesis of both luciferase reporters, indicating a condition where general translation is not disturbed.

The original deletion strains corresponding to these candidate modulator strains will be used to receive a firefly luciferase reporter harboring the target mRNA coding sequence and the *Renilla* luciferase reporter. Translational readout via measurements of luciferase activities will determine whether translation of the target mRNA coding sequence changes the firefly luciferase read out, but not the *Renilla* luciferase read out. In parallel, as an internal control, overall amount of protein produced (per volume of culture, per cell) may be determined. If so, the invention has identified a condition where the translation of a given target mRNA—harboring disease/undesirable condition-conferring alterations/mutations in the mRNA coding and/or regulatory region—is increased or decreased.

In sum, the present invention offers to industry, medicine and academia a fast and affordable in vivo assay to test the contribution of ribosomal protein gene deletions to modulation of translation of protein encoded by a given target mRNA, for example those with mutations in the coding and regulatory region.

Construction and Use of the Modular In Vitro Dual Luciferase Reporter Assay to Monitor Differential mRNA Translation Mediated by Mutant Ribosomal Proteins 1. Reporter Components
1.1 Parent Vectors The vectors YCplac 33 (pLBK 001, ATCC 87586), harbouring the ura3 selective marker, and YCplac 111 (pLBK 003, ATCC 87587), harbouring the leu2 selective marker, were used. (Gietz and Sugino, 1988). The sequences of the plasmids and the maps thereof can be downloaded from the LGC Standards (LGC Standards GmbH, Wesel, Germany) homepage.

1.2 Reporter Sequences
1.2.1 ADH1 Promoter and Terminator pGBKT7 of 7.3 kb was the vector used in yeast Two-Hybrid Systems (Clontech, Mountain View, CA, USA). It contains a truncated but functional yeast ADH1 promoter and terminator. The sequence and the map of said vector can be downloaded from the Clontech homepage. The ADH1 promoter and terminator were selected to provide expression during exponential growth of yeast cells (Smidt et al., 2008).

1.2.2 Firefly Luciferase Reporter

The Firefly luciferase vector pGL4.10 (Promega, Madison, WI, USA) was used: The luc2 (firefly luciferase) reporter is synthetically engineered from *Photinus pyralis*. The firefly luciferase encodes for a 61 kDa monomeric protein that does not need any post translational processing, therefore starting its function directly upon translation. By the oxidation of beetle luciferin in the presence of ATP, $Mg^{2+}$ and $O_2$ to oxyluciferin amongst others light is emitted. A "flash" is generated to be measured. Information on the vector and the map are to be found in Promega TM 259 (2008) and TM 040 (2005).

1.2.3 *Renilla* Luciferase Reporter

*Renilla* luciferase vector pGL4.75 (Promega, Madison, WI, USA): The hRluc (*Renilla luciferase*) reporter is synthetically engineered from *Renilla reniformis*, also known as sea pansy. The *Renilla* luciferase encodes for a 36 kDa monomeric protein that does not need any post translational processing, therefore starting its function directly upon translation. In the presence of the *Renilla* luciferase coelenterazine (coelenterate luciferin) is catalysed in the presence of $O_2$ to coelenteramide and light that is measured. Information on the vector and the map are to be found in Promega TM 259 (2008) and TM 040 (2005).

1.2.4 CYH2-PTC-Reporter (see FIG. 5a)

CYH2 is a well characterised PTC reporter for testing the PTC-mRNA stability. The unspliced CYH2 pre-mRNA, 961 bp, coding for RPL28, has an intron of 510 bp harbouring several PTCs. (Kaufer et al., 1983). The complete gene sequence can be found at the *Saccharomyces* Genome Database homepage.

2. Generation of Individual Components of the Reporter Plasmids
2.1 The Firefly Reporter Plasmid
2.1.1 The ADH1 Promoter Sequence The ADH1 promoter was amplified from the pGBKT7 using suitable primers. pGBKT7 has a truncated ADH1 promoter, missing 17 nt. The missing sequence, including the start codon, was restored with the reverse primer. The 0.75 kb PCR product and YCplac 33 were digested with Hind III and PstI. The ADH1 promoter was ligated into YCplac 33, generating pLBK 160 (FIG. 5b).

2.1.2 The ADH1 Terminator Sequence

The ADH1 terminator was amplified from the pGBKT7 using suitable primers. Two silent point mutations in the reverse primer eliminated two restriction sites in the end of the terminator. The 0.3 kb PCR product and the pLM 160 were digested with SacI and EcoRI. The ADH1 terminator was ligated in pLBK 160, making pLBK 161 (FIG. 5c).

2.1.3 The Firefly Sequence

The firefly luciferase reporter was amplified from pGL 4.10 with the primers LG 735 and LG 736. The ATG of the firefly was left out to be in frame with the ADH1 promoter and for constructs inserted later upstream of the firefly luciferase. The 1.6 kb PCR product and pLBK 161 were digested with KpnI and SacI. The firefly luciferase was ligated in pLBK 161, generating pLBK 162 (FIG. 5d).

pLBK 162 was generated to function as a carrier for the PTC containing genes, e.g. CYH2. With this approach, the restriction sites PstI, SalI, XbaI, BamHI, SmaI and KpnI were conserved for further cloning.

2.2 The *Renilla* Reporter Plasmid

The *Renilla* luciferase reporter was amplified from pGL 4.75 with suitable primers. The ATG of the *Renilla* was left out to be in frame with the ADH1 promoter. The 1 kb PCR product and pLBK 161 were digested with XbaI and SacI (=pLBK 163). In the next step, the YCplac 111 and pLBK 163 were digested with Hind III and EcoRI. The ADH1 promoter-*Renilla*-ADH1 terminator cassette from pLBK 163 was ligated with the digested YCplac 111 resulting in pLBK 164 (FIG. 5e).

PLBK 164 was generated to function as an internal standard in the co-transformation with the firefly-containing plasmid. For cloning the *Renilla* luciferase the restriction sites XbaI and SacI were chosen to eliminate as many restriction sites as possible, so to shorten the MCS that downstream of the ATG from the promoter the *Renilla* luciferase can directly be expressed.

2.3. PTC Reporter Plasmids and Control Plasmids 2.3.1 The CYH2-Firefly Reporter Plasmid The yeast CYH2 was amplified from the genomic yeast DNA with the primers LG 751 and LG 752. The ATG of the CYH2 was left out to be in frame with the promoter and the firefly luciferase reporter. The 1.0 kb PCR product and pLBK 162 were digested with KpnI and SacI. The CYH2-PTC reporter was ligated in pLBK 162, thus generating pLBK 165 (FIG. 5f).

2.3.2 The FF(PTC) Reporter Plasmid

The PTC mutation was introduced into the Firefly luciferase of pLBK 162 with primers LG 831 and LG 832 at nt 159, where a tyrosin codon was changed to a stop codon (UAC-→UAA), thus generating pLBK 167.

2.3.3 The LAMB3-FF Reporter Plasmid

The laminin B3 was amplified from a suitable cDNA sample, using primers LG 825 and LG 826. The 3.5 kb PCR product was cloned into pLBK 162 with restriction sites XbaI and KpnI, generating pLBK 168

2.3.4 The LAMB3(PTC)-FF Reporter Plasmid

The mutant PTC was introduced into the laminin B3 gene of pLBK 168 with primers LG 847 and LG 848, to change nt 1903, in order to change an arginine codon into a stop codon (CGA 4 TGA), thus generating pLBK 169.

2.4. Transformation of the Reporter Plasmids in Yeast WT and RP Deletion Strains 2.4.1 Yeast Strains Yeast strains were obtained from the EUROSCARF deletion strain collection. As reference the diploid yeast strain BY4743=wild type (WT) (MATa/MATα; his3/his3; leu2/leu2; met15/MET15; LYS2/lys2; ura3/ura3) was used.

In the collection, 6138 ORFs were replaced with an antibiotic resistance cassette, KanMX4, using PCR. (Kelly, Lamb et al. 2001) In the present experiments, the systematic name of the strain RPL10/RPL10, would be, for example, BY4743; YLR075W (RPL10)::kanMX4. The systematic names of the respective genes can be found on the *Saccharomyces* Genome Database homepage.

TABLE 1

Ribosomal deletion strains.

| Standard name | systematic name |
|---|---|
| WT, diploid | WT |
| Large Subunit: | |
| RPP0 | YLR340W |
| RPP1A | YDL081C |
| RPP1B | YDL130W |
| RPP2A | YOL039W |
| RPP2B | YDR382W |
| RPL1A | YPL220W |
| RPL1B | YGL135W |
| RPL2A | YFR031C-A |
| RPL2B | YIL018W |
| RPL3 | YOR063W |
| RPL4A | YBR031W |
| RPL4B | YDR012W |
| RPL5 | YPL131W |
| RPL6A | YML073C |
| RPL6B | YLR448W |
| RPL7A | YGL076C |
| RPL7B | YPL198W |
| RPL8A | YHL033C |
| RPL8B | YLL045C |
| RPL9A | YGL147C |
| RPL9B | YNL067W |
| RPL10 | YLR075W |

TABLE 1-continued

Ribosomal deletion strains.

| Standard name | systematic name |
|---|---|
| WT, diploid | WT |
| RPL11A | YPR102C |
| PRL11B | YGR085C |
| RPL12A | YEL054C |
| RPL12B | YDR418W |
| RPL13A | YDL082W |
| RPL13B | YMR142C |
| RPL14A | YKL006W |
| RPL14B | YHL001W |
| RPL15A | YLR029C |
| RPL15B | YMR121C |
| RPL16A | YIL133C |
| RPL16B | YNL069C |
| RPL17A | YKL180W |
| RPL17B | YJL177W |
| RPL18A | YOL120C |
| RPL18B | YNL301C |
| RPL19A | YBR084C-A |
| RPL19B | YBL027W |
| RPL20A | YMR242C |
| RPL20B | YOR312C |
| RPL21A | YBR191W |
| RPL21B | YPL079W |
| RPL22A | YLR061W |
| RPL22B | YFL034C-A |
| RPL23A | YBL087C |
| RPL23B | YER117W |
| RPL24A | YGL031C |
| RPL24B | YGR148C |
| RPL25 | YOL127W |
| RPL26A | YLR344W |
| RPL26B | YGR034W |
| RPL27A | YHR010W |
| RPL27B | YDR471W |
| RPL28 | YGL103W |
| RPL29 | YFR032C-A |
| RPL30 | YGL030W |
| RPL31A | YDL075W |
| RPL31B | YLR406C |
| RPL32 | YBL092W |
| RPL33A | YPL143W |
| RPL33B | YOR234C |
| RPL34A | YER056C-A |
| RPL34B | YIL052C |
| RPL35A | YDL191W |
| RPL35B | YDL136W |
| RPL36A | YMR194W |
| RPL36B | YPL249C-A |
| RPL37A | YLR185W |
| RPL37B | YDR500C |
| RPL38 | YLR325C |
| RPL39 | YJL189W |
| RPL40A | YIL148W |
| RPL40B | YKR094C |
| RPL41A | YDL184C |
| RPL41B | YDL133C-A |
| RPL42A | YNL162W |
| RPL42B | YHR141C |
| RPL43A | YPR043W |
| RPL43B | YJR094W-A |
| Small subunit: | |
| RPS0A | YGR214W |
| RPS0B | YLR048W |
| RPS1A | YLR441C |
| RPS1B | YML063W |
| RPS2 | YGL123W |
| RPS3 | YNL178W |
| RPS4A | YJR145C |
| RPS4B | YHR203C |
| RPS5 | YJR123W |
| RPS6A | YPL090C |
| RPS6B | YBR181C |
| RPS7A | YOR096W |
| PRS7B | YNL096C |
| RPS8A | YBL072C |

TABLE 1-continued

Ribosomal deletion strains.

| Standard name WT, diploid | systematic name WT |
|---|---|
| RPS8B | YER102W |
| RPS9A | YPL081W |
| RPS9B | YBR189W |
| RPS10A | YOR293W |
| RPS10B | YMR230W |
| RPS11A | YDR025W |
| RPS11B | YBR048W |
| RPS12 | YOR369C |
| RPS13 | YDR064W |
| RPS14A | YCR031C |
| RPS14B | YJL191W |
| RPS15 | YOL040C |
| RPS16A | YMR143W |
| RPS16B | YDL083C |
| PRS17A | YML024W |
| RPS17B | YDR447C |
| RPS18A | YDR450W |
| RPS18B | YML026C |
| RPS19A | YOL121C |
| RPS19B | YNL302C |
| RPS20 | YHL015W |
| RPS21A | YKR057W |
| RPS21B | YJL136C |
| RPS22A | YJL190C |
| RPS22B | YLR367W |
| RPS23A | YGR118W |
| RPS23B | YPR132W |
| RPS24A | YER074W |
| RPS24B | YIL069C |
| RPS25A | YGR027C |
| RPS25B | YLR333C |
| RPS26A | YGL189C |
| RPS26B | YER131W |
| RPS27A | YKL156W |
| RPS27B | YHR021C |
| RPS28A | YOR167C |
| RPS28B | YLR264W |
| RPS29A | YLR388W |
| RPS29B | YDL061C |
| RPS30A | YLR287C-A |
| RPS30B | YOR182C |
| RPS31 | YLR167W |

2.4.2 Transformation Procedure

The Firefly containing reporter and the *Renilla* reporter, as internal standard, were co-transformed in yeast strains as described in "Current Protocols in Molecular Biology" by Ausubel et al., 1998.

2.4.3 Strains as Transformed

The reporter plasmids are to be transformed in the WT and ribosomal protein deletion strains. For general expression studies pLBK 162 and pLBK 164 are used. For testing the different levels of read-through a PTC containing reporter plasmid (e.g. pLBK 165) and for internal standard pLBK 164 are used. A list of the ribosomal protein deletion strains in which the constructs are tested, is found in table 1.

3. Luciferase Measurements 3.1 Precision of the Assay System (FIG. 2)

FIG. 2 shows the precision of the assay system as used herein. As an example, pLBK 162 (FF) and 164 (R) were transformed in the WT (FIG. 2A). Luminescence measurements were performed three times with a double measurement. The three results of the double measurements and the median values of the results, including the deviations are depicted.

In FIG. 2B, six individual dual luciferase measurements of the FF/FF-PTC reporter system are shown. Specifically, dual luciferase analyses of plasmids pLBK 162 (FF)/pLBK 164 (R), shown in FIG. 2B1 and pLBK 166 (FF-PTC)/pLBK 164 (R), shown in FIG. 2B2, respectively, including their mean value plus standard deviation are reported. In FIG. 2C, six individual dual luciferase measurements of the LAMB3-FF/LAMB3(PTC)-FF reporter system are shown. Specifically, dual luciferase analyses of plasmids pLBK 168 (LAMB3-FF)/pLBK 164 (R), shown in FIG. 2C1, and pLBK 169 (LAMB3(PTC)-FF)/pLBK 164 (R), shown in FIG. 2C2, respectively are reported, including their mean value plus standard deviation.

3.2 Functionality of PTC Reporter (FIG. 3)

FIG. 3A: To test the functionality of the CYH2-PTC reporter, pLBK 165 (CYH2-PTC-FF) and 164 (R) and on the other hand pLBK 162 (FF) and 164 (R) were transformed into WT and RPL10/ΔRPL10, respectively. A reduction of the Firefly CYH2-PTC signal is observed in both strains, however the RPL10/ΔRPL10 condition does not decrease the signal as much as the WT, thus showing increased CYH2-PTC protein expression. As a control gentamycin was shown to induce an increase of the CYH2-PTC-FF level in the WT, however in the RPL10/ΔRPL10 condition gentamycin does not contribute to alteration of the expression level of the CYH2-PTC-FF reporter.

FIG. 3B shows the functionality for the FF/FF-PTC system. A decrease of FF-PTC signal—ranging from two to ten-fold—is observed in a selected set of ribosomal protein deletion strains. This first set of candidate ribosomal protein deletion strains consists of RPL10/ΔRPL10, RPL4A/ΔRPL4A and RPL25/ΔRPL25. FIG. 3C shows the functionality of the LAMB3-FF/LAMB3(PTC)-FF system. In this system, Firefly signal of the wild type LAMB3-FF construct is lower than that of the parent FF reporter (compare FIGS. 2 B and 2 C). However, the LAMB3-PTC reporter is clearly functional. A first set of candidate ribosomal protein deletion strains is presented, RPL10/ΔRPL10, RPL4A/ΔRPL4A RPL25/ΔRPL25 and RPL 19A/ΔRPL19A. The LAMB3-PTC-FF reporter in RPL19A/ΔRPL19A has a five fold higher protein expression level, when compared to WT. This observation is of particular interest to strategies aiming to increase the protein expression from disease associated PTC mRNAs.

4. Further Experimental Strategies

The PTC containing construct (e.g. CYH2) decreases the amount of firefly luminescence counts, compared to the reporter without PTC constructs (for an overview, see FIG. 1), and this principle can also be used to generate other PTC reporters. Using this experimental strategy, strains with ribosomal protein deletions and/or mutations can be identified that alter the amount of the reduced firefly signals by the PTC containing reporter. Then, this system can be used in order to screen for compounds or mutations of ribosomal proteins that revert or at least partially revert the reduced (or even increased) expression of the mRNA as analyzed. In other words, although the present experiments have been performed for an analysis of mRNAs with premature termination codons, this system can also be modified and used in order to analyse other mRNA populations that show a modified expression upon changes in the ribosomal proteins. The person of skill, when reading the teaching of the present invention as herein, will be readily able to modify the system(s) as required for these purposes using regular techniques of molecular biology.

BACKGROUND LITERATURE

Bogengruber, E., Briza, P., Doppler, E., Wimmer, H., Koller, L., Fasiolo, F., Senger, B., Hegemann, J. H. and Breitenbach, M. (2003). Functional analysis in yeast of the Brix protein super-family involved in the biogenesis of ribosomes. FEMS Yeast Res 3, 35-43.

Chiocchetti, A., Zhou, J., Zhu, H., Karl, T., Haubenreisser, O., Rinnerthaler, M., Heeren, G., Oender, K., Bauer, J., Hintner, H., Breitenbach, M. and Breitenbach-Koller, L. (2007). Ribosomal proteins Rpl10 and Rps6 are potent regulators of yeast replicative life span. Exp Gerontol 42, 275-86.

Klauck, S. M., Felder, B., Kolb-Kokocinski, A., Schuster, C., Chiocchetti, A., Schupp, I., Wellenreuther, R., Schmotzer, G., Poustka, F., Breitenbach-Koller, L. and Poustka, A. (2006). Mutations in the ribosomal protein gene RPL10 suggest a novel modulating disease mechanism for autism. Mol Psychiatry 11, 1073-84.

Laun, P., Heeren, G., Rinnerthaler, M., Rid, R., Kossler, S., Koller, L. and Breitenbach, M. (2008). Senescence and apoptosis in yeast mother cell-specific aging and in higher cells: a short review. Biochim Biophys Acta 1783, 1328-34.

Oender, K., Loeffler, M., Doppler, E., Eder, M., Lach, S., Heinrich, F., Karl, T., Moesl, R., Hundsberger, H., Klade, T., Eckl, P., Dickinson, J. R., Breitenbach, M. and Koller, L. (2003). Translational regulator RpL10p/Grc5p interacts physically and functionally with Sed1p, a dynamic component of the yeast cell surface. Yeast 20, 281-94.

Pachler, K., Karl, T., Kolmann, K., Mehlmer, N., Eder, M., Loeffler, M., Oender, K., Hochleitner, E. O., Lottspeich, F., Bresgen, N., Richter, K., Breitenbach, M. and Koller, L. (2004). Functional interaction in establishment of ribosomal integrity between small subunit protein rpS6 and translational regulator rpL10/Grc5p. FEMS Yeast Res 5, 271-80.

Rinnerthaler, M., Jarolim, S., Heeren, G., Palle, E., Perju, S., Klinger, H., Bogengruber, E., Madeo, F., Braun, R. J., Breitenbach-Koller, L., Breitenbach, M. and Laun, P. (2006). MMI1 (YKL056c, TMA19), the yeast orthologue of the translationally controlled tumor protein (TCTP) has apoptotic functions and interacts with both microtubules and mitochondria. Biochim Biophys Acta 1757, 631-8.

Bauer J W, et al. Gene therapy of epidermolysis bullosa. Expert Opin Biol Ther (2004) 4: 1435-1443

Bauer J W, et al. Highly sensitive dsDNA quantitation using fluorescence. Am Biotechnol Laboratory (2004) 22(13): 16-19

Bauer J W, et al. Current approaches to cutaneous gene therapy. Expert Review in Dermatology (2006) 1: 833-855

Bauer J W, et al. Epidermolysis bullosa hereditaria. Monatsschr Kinderheilkd (2008) 156: 110-115

Bauer J W, et al. Galanin family of peptides in skin function. Cell Mol Life Sci (2008) 65:1820-5

Bauer J W, et al. Mutation analysis. In: Life with Epidermolysis bullosa (EB): Etiology, Diagnosis, Multidisciplinary Care and Therapy. Ed.: Hintner H, Fine J D. Springer Berlin, Wien, New York (2008) 54-64

Bauer J W, et al. Genetic counselling. In: Life with Epidermolysis bullosa (EB): Etiology, Diagnosis, Multidisciplinary Care and Therapy. Ed.: Hintner H, Fine J D. Springer Berlin, Wien, New York (2008) 89-98

Bauer J W, et al. Molecular therapy of epidermolysis bullosa. In: Life with Epidermolysis bullosa (EB): Etiology, Diagnosis, Multidisciplinary Care and Therapy. Ed.: Hintner H, Fine J D. Springer Berlin, Wien, New York (2008) 287-310

Fine J D, Eady R A, Bauer E A, Bauer J W, Bruckner-Tuderman L, Heagerty A, Hintner H, Hovnanian A, Jonkman M F, Leigh I, McGrath J A, Mellerio J E, Murrell D F, Shimizu H, Uitto J, Vahlquist A, Woodley D, Zambruno G. The classification of inherited epidermolysis bullosa (EB): Report of the Third International Consensus Meeting on Diagnosis and Classification of EB. J Am Acad Dermatol. 2008 June; 58(6):931-50. Epub 2008 Apr. 18.

Wally V, Klausegger A, Koller U, Lochmüller H, Krause S, Wiche G, Mitchell L G, Hintner H, Bauer J W. 5' trans-splicing repair of the PLEC1 gene. J Invest Dermatol. 2008 March; 128(3):568-74. Epub 2007 Nov. 8.

Sadler E, Schafleitner B, Lanschuetzer C, Laimer M, Pohla-Gubo G, Hametner R, Hintner H, Bauer J W. Treatment-resistant classical epidermolysis bullosa acquisita responding to rituximab. Br J. Dermatol. 2007 August; 157(2):417-9. Epub 2007 Jun. 26. No abstract available.

Nischler C, Sadler E, Lazarova Z, Stoiber J, Ruckhofer J, Pohla-Gubo G, Emberger M, Bauer J W, Grabner G, Hintner H. Ocular involvement in anti-epiligrin cicatricial pemphigoid. Eur J Ophthalmol. 2006 November-December; 16(6):867-9.

Sadler E, Klausegger A, Muss W, Deinsberger U, Pohla-Gubo G, Laimer M, Lanschuetzer C, Bauer J W, Hintner H. Novel KIND1 gene mutation in Kindler syndrome with severe gastrointestinal tract involvement. Arch Dermatol. 2006 December; 142(12):1619-24.

Sadler E, Laimer M, Diem A, Klausegger A, Pohla-Gubo G, Muss W, Hachleitner J, Stadlhuber R, Bauer J W, Hintner H. [Dental alterations in junctional epidermolysis bullosa—report of a patient with a mutation in the LAMB3-gene] J Dtsch Dermatol Ges. 2005 May; 3(5): 359-63. German.

Lanschuetzer C M, Emberger M, Laimer M, Diem A, Bauer J W, Soyer H P, Hintner H. Epidermolysis bullosa naevi reveal a distinctive dermoscopic pattern. Br J. Dermatol. 2005 July; 153(1):97-102.

Buchroithner B, Klausegger A, Ebschner U, Anton-Lamprecht I, Pohla-Gubo G, Lanschuetzer C M, Laimer M, Hintner H, Bauer J W. Analysis of the LAMB3 gene in a junctional epidermolysis bullosa patient reveals exonic splicing and allele-specific nonsense-mediated mRNA decay. Lab Invest 2004 (10): 1279-88

Lanschuetzer C M, Emberger M, Hametner R, Klausegger A, Pohla-Gubo G, Hintner H, Bauer J W. Pathogenic mechanisms in epidermolysis bullosa naevi. Acta Derm Venereol. 2003; 83(5):332-7.

Dallinger G, Puttaraju M, Mitchell L G, Yancey K B, Yee C, Klausegger A, Hintner H, Bauer J W. Development of spliceosome-mediated RNA trans-splicing (SMaRT) for the correction of inherited skin diseases. Exp Dermatol. 2003 February; 12(1):37-46.

Lanschuetzer C M, Klausegger A, Pohla-Gubo G, Hametner R, Richard G, Uitto J, Hintner H, Bauer J W. A novel homozygous nonsense deletion/insertion mutation in the keratin 14 gene (Y248X; 744delC/insAG) causes recessive epidermolysis bullosa simplex type Kšbner. Clin Exp Dermatol. 2003 January; 28(1):77-9.

Weber F, Bauer J W, Sepp N, Hogler W, Salmhofer W, Hintner H, Fritsch P. Squamous cell carcinoma in junctional and dystrophic epidermolysis bullosa. Acta Derm Venereol. 2001 June-July; 81(3):189-92.

Bauer J W, Schaeppi H, Kaserer C, Hantich B, Hintner H. Large melanocytic nevi in hereditary epidermolysis bullosa. J Am Acad Dermatol. 2001 April; 44(4):577-84.

The invention claimed is:

1. A screening system for a compound that ameliorates or reverts a defective or undesired translational read-through of a target gene bearing a premature termination codon (PTC) in a eukaryotic cell, the screening system comprising a recombinant eukaryotic cell
   a) expressing a recombinant ribosome comprising a ribosomal protein having a deletion or other mutation that causes a defective or undesired translational read-through of a PTC-bearing target gene,
   b) expressing a first reporter construct comprising said PTC-bearing target gene coupled to a gene encoding a first reporter group that is co-expressed with said PTC-bearing target gene,
   c) expressing a second reporter construct comprising a gene encoding a second reporter group that is expressed independently from said PTC-bearing target gene as an internal standard,
   wherein the first reporter construct and the second reporter construct are both expression cassettes or both expression vectors,
   wherein said first and second reporter groups are independently selected from fluorescent protein reporter molecules, bioluminescent protein reporter molecules, maltose binding protein, phosphatase, peroxidase, kinase, chloramphenicol transferase, and β-galactosidase,
   wherein said PTC-bearing target gene is selected from the group consisting of a LAMB3 gene and a CYH2 gene, and
   wherein said ribosomal protein is selected from the group consisting of rPL19A, rPL25, and rPL10.

2. The screening system according to claim 1, wherein said PTC-bearing target gene encodes a protein that causes epidermolysis bullosa.

3. A method for identifying a compound that ameliorates or reverts a defective or undesired translational read-through of a target gene bearing a premature termination codon (PTC) in a eukaryotic cell, said method comprising:
   a) contacting a screening system according to claim 1 with a compound that potentially ameliorates or reverts the defective or undesired translational read-through of a target gene bearing a premature termination codon (PTC),
   b) measuring the expression of a first reporter group in the presence and absence of said compound, and
   c) measuring the expression of a second reporter group in the presence and absence of said compound as an internal standard;
      wherein a compound that ameliorates or reverts a defective or undesired translational read-through of said PTC-bearing target gene is identified by
         i) a change in the expression of said first reporter group in the presence of said compound compared to the expression of said first reporter group in the absence of said compound and
         ii) the absence of a change in the expression of said second reporter group in the presence of said compound compared to the expression of said second reporter group in the absence of said compound.

4. A kit for identifying a compound that ameliorates or reverts a defective or undesired translation of a target gene bearing a premature termination codon (PTC), comprising a) a recombinant eukaryotic cell comprising a ribosomal protein deletion or other mutation that causes said defective or undesired translation of a PTC-bearing target gene wherein said ribosomal protein is selected from the group consisting of rPL19A, rPL25, and rPL10, b) a receptor plasmid comprising a PTC-bearing target gene selected from the group consisting of a LAMB3 gene and a CYH2 gene that is inserted in frame with and upstream of a first reporter group and a control plasmid harboring a second reporter group, c) instructions for practicing a method of identifying a compound that ameliorates or reverts a defective translation of the PTC-bearing target gene.

5. The screening system of claim 1, wherein the fluorescent protein reporter molecule is green fluorescent protein.

6. The screening system of claim 1, wherein the bioluminescent protein reporter molecule is *Renilla* luciferase, firefly luciferase or an internal tryptophan reporter group.

7. The screening system according to claim 1, wherein said ribosomal protein deletion or other mutation does not directly influence ribosome binding to a tRNA or a rRNA structure.

8. The screening system according to claim 1, wherein said target gene bearing a PTC is a LAMB3 gene and said ribosomal protein is rPL19A.

9. The screening system according to claim 1, wherein said target gene bearing a PTC is a CYH2 gene and said ribosomal protein is rPL10.

10. The screening system according to claim 1, wherein said target gene bearing a PTC is a LAMB3 gene and said ribosomal protein is rPL25.

* * * * *

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: PTC example sequence

<400> SEQUENCE: 1
cttagtgact acggttataa acct                                              24

<210> SEQ ID NO 2
<211> LENGTH: 24
<212> TYPE: DNA
<213> ORGANISM: Artificial Sequence
<220> FEATURE:
<223> OTHER INFORMATION: PTC example sequence reverse

<400> SEQUENCE: 2
aggtttataa ccgtagtcac taag                                              24

<210> SEQ ID NO 3
<211> LENGTH: 8
<212> TYPE: PRT
<213> ORGANISM: Artificial Sequence
<220> FEATURE:
<223> OTHER INFORMATION: PTC sequence translated

<400> SEQUENCE: 3

Leu Ser Asp Tyr Gly Tyr Lys Leu
1               5